(12) United States Patent
Nakahashi et al.

(10) Patent No.: US 8,853,644 B2
(45) Date of Patent: Oct. 7, 2014

(54) RADIATION IMAGE CAPTURE DEVICE

(71) Applicant: FUJIFILM Corporation, Tokyo (JP)

(72) Inventors: Hiroshi Nakahashi, Kanagawa (JP);
Keiichiro Sato, Kanagawa (JP);
Haruyasu Nakatsugawa, Kanawaga (JP)

(73) Assignee: FUJIFILM Corporation, Tokyo (JP)

( * ) Notice: Subject to any disclaimer, the term of this patent is extended or adjusted under 35 U.S.C. 154(b) by 158 days.

(21) Appl. No.: 13/653,290

(22) Filed: Oct. 16, 2012

(65) Prior Publication Data

US 2013/0099130 A1    Apr. 25, 2013

(30) Foreign Application Priority Data

Oct. 19, 2011    (JP) .................. 2011-230076

(51) Int. Cl.
*G01J 1/42* (2006.01)
*A61B 6/00* (2006.01)

(52) U.S. Cl.
CPC *A61B 6/00* (2013.01); *A61B 6/4208* (2013.01)
USPC ........................................................ 250/394

(58) Field of Classification Search
CPC .............. G01T 1/00; G01T 1/20; G01T 1/202; G01T 1/24
USPC ................. 250/394, 370.01–370.15
See application file for complete search history.

(56) References Cited

U.S. PATENT DOCUMENTS 7,053,379 B2 *  5/2006  Watanabe ................. 250/370.09
7,210,847 B2 *  5/2007  Hack ............................ 378/189
7,796,735 B2 *  9/2010  Yi .................................. 378/98.8
2002/0181659 A1  12/2002  Watanabe et al.
2006/0171507 A1   8/2006  Watanabe et al.
2007/0165785 A1   7/2007  Watanabe et al.

(Continued)

FOREIGN PATENT DOCUMENTS

JP    5-259591 A    10/1993
JP    2002-158341 A    5/2002

(Continued)

OTHER PUBLICATIONS

Notification of Reason(s) for Rejection dated Oct. 8, 2013, with English translation.

(Continued)

*Primary Examiner* — Kiho Kim
(74) *Attorney, Agent, or Firm* — McGinn IP Law Group, PLLC

(57) ABSTRACT

A radiation image capture device is provided with a radiation detection panel, a signal processing board, a flexible printed circuit, a casing, and a first conductor. The radiation detection panel includes optoelectronic conversion elements that convert radiation to electronic signals. The signal processing board is disposed to oppose the radiation detection panel and performs signal processing of the electronic signals provided by the radiation detection panel. One end of the flexible printed circuit is electrically connected to the radiation detection panel and the other end is electrically connected to the signal processing board. The casing accommodates the radiation detection panel and the signal processing board, and accommodates the flexible printed circuit in a state of being separated from inner walls of the casing. The first conductor is provided at a region of the flexible printed circuit that comes in contact with the casing by movements of the flexible printed circuit.

20 Claims, 13 Drawing Sheets

(56) References Cited

U.S. PATENT DOCUMENTS

| | | | |
|---|---|---|---|
| 2012/0074331 A1* | 3/2012 | Koyanagi | 250/394 |
| 2013/0153780 A1* | 6/2013 | Lee et al. | 250/394 |
| 2013/0292577 A1* | 11/2013 | Lee et al. | 250/394 |

FOREIGN PATENT DOCUMENTS

| | | |
|---|---|---|
| JP | 2004-246384 (A) | 9/2004 |
| JP | 2005-308409 (A) | 11/2005 |
| JP | 2009-257914 A | 11/2009 |
| JP | 2010-264250 A | 11/2010 |
| JP | 2011-95166 A | 5/2011 |

OTHER PUBLICATIONS

Notification of Reason(s) for Rejection dated Jul. 1, 2014, with English translation.

\* cited by examiner

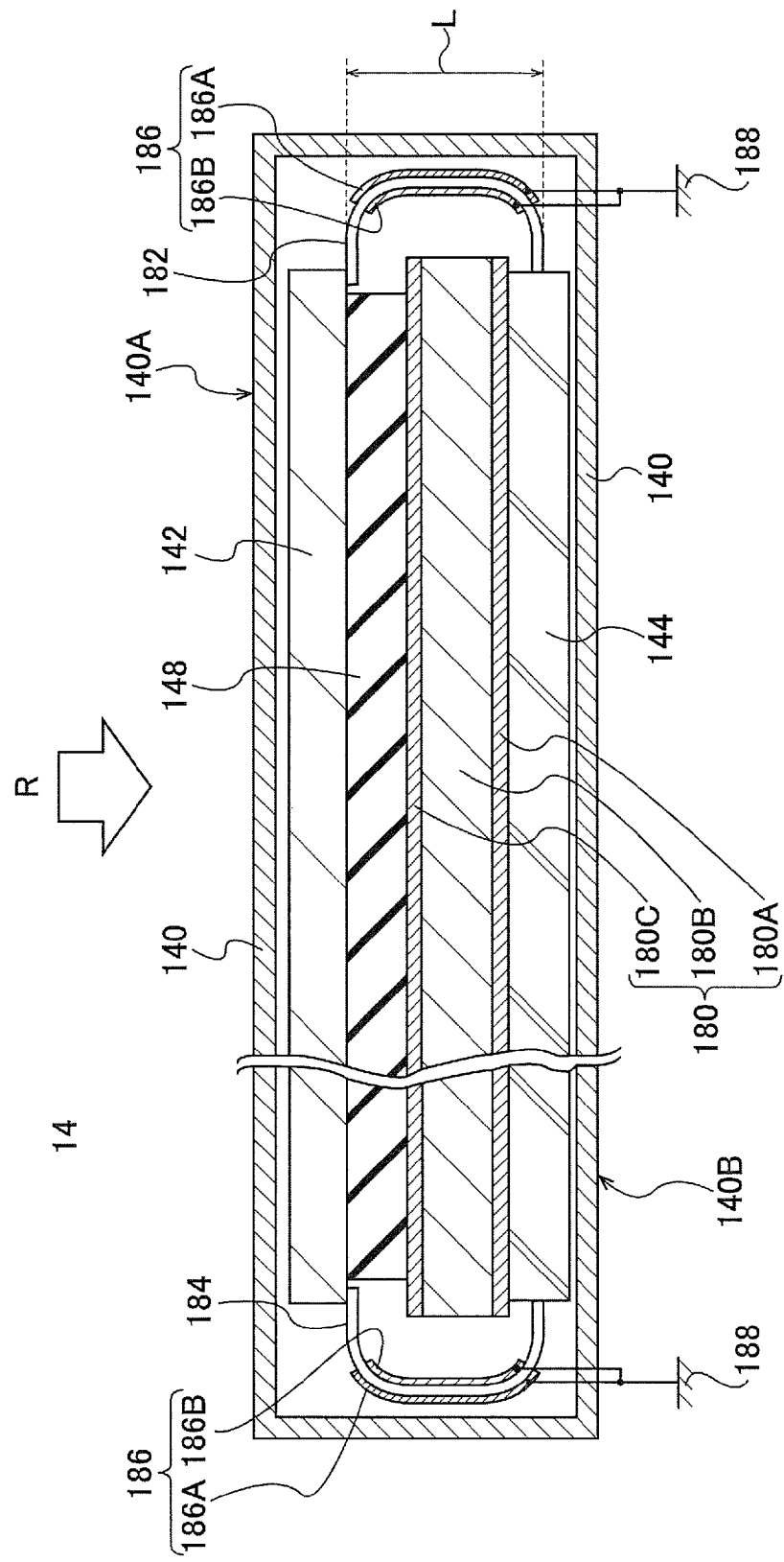

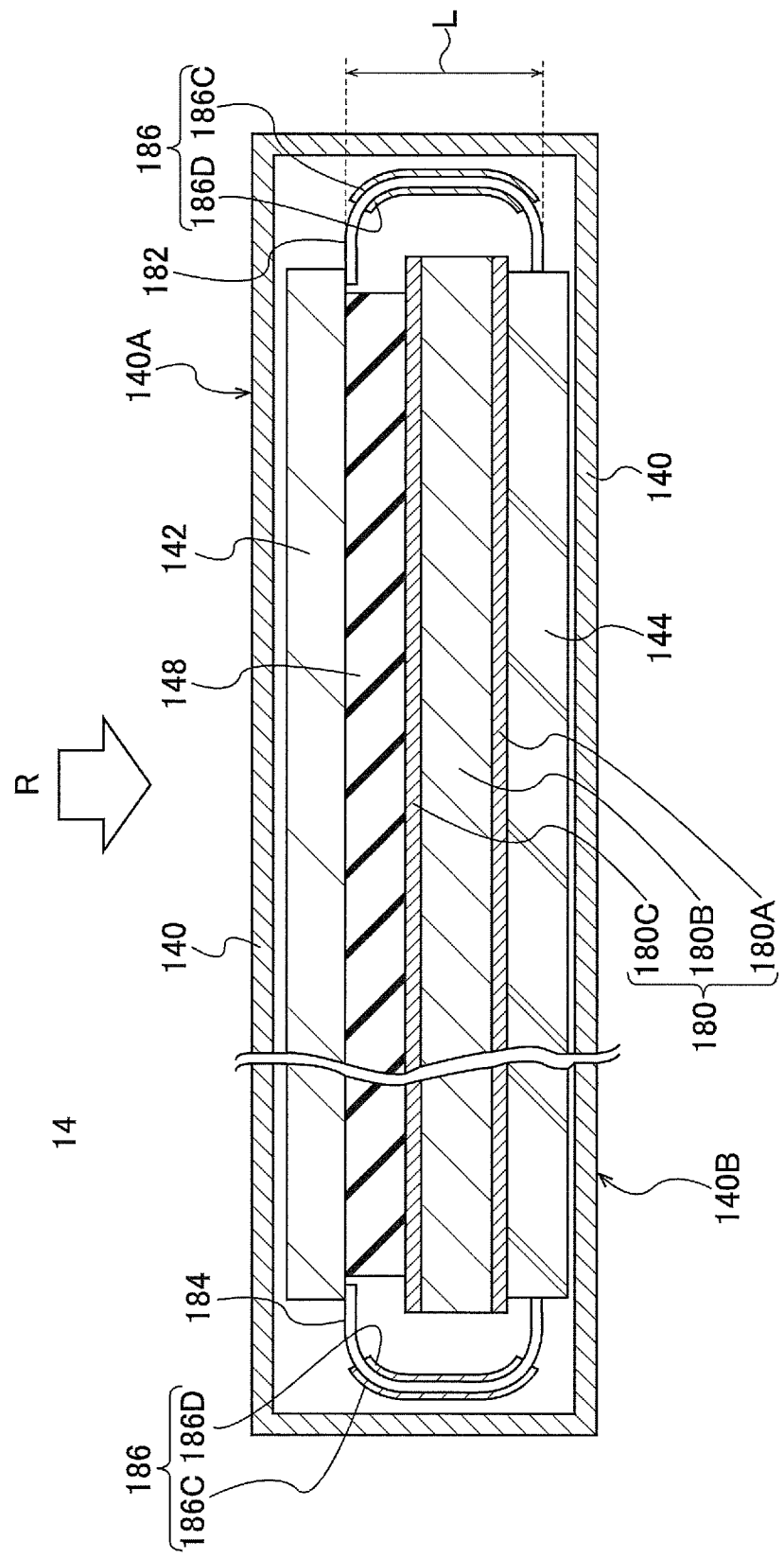

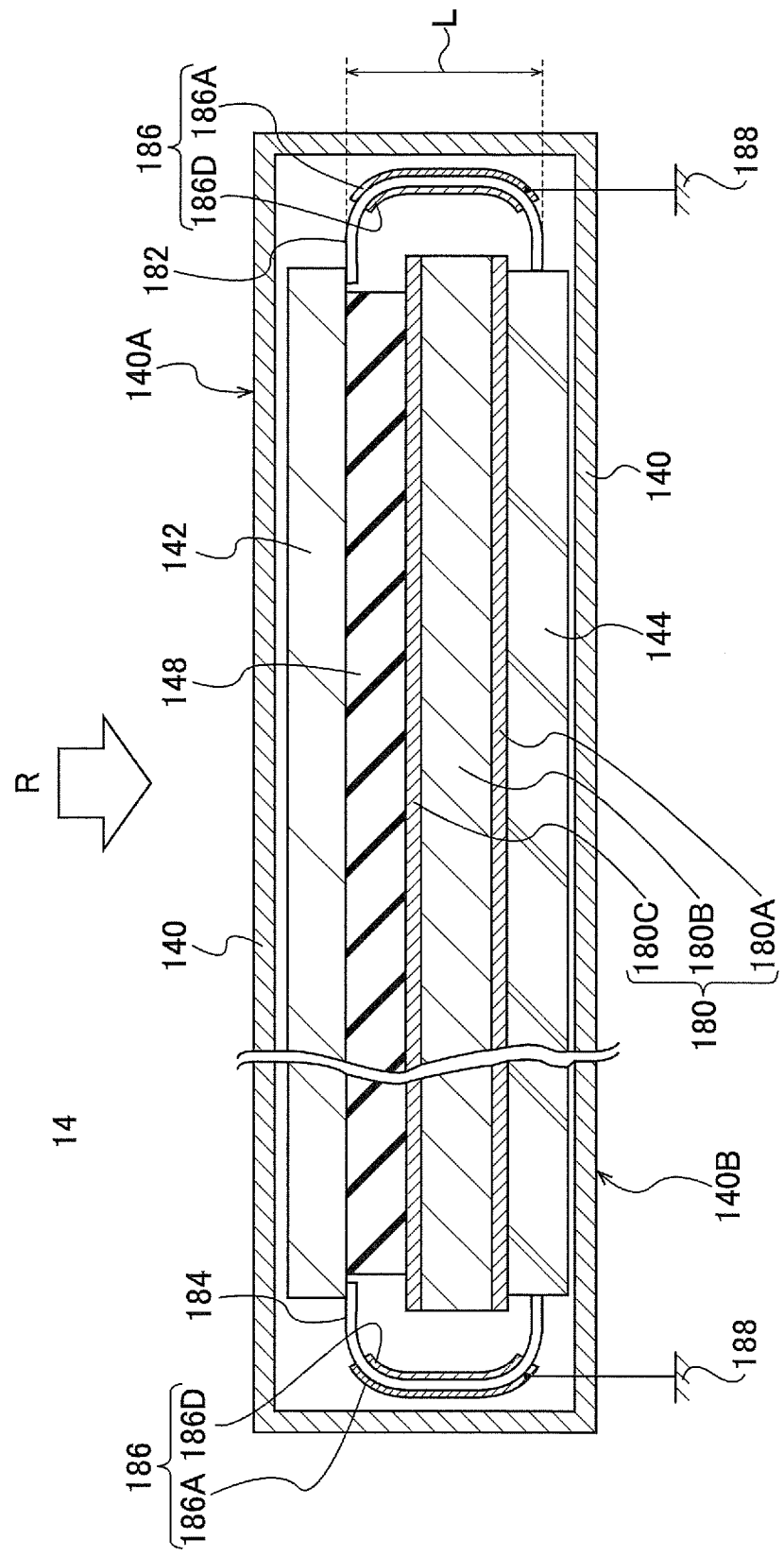

RADIATION IMAGE CAPTURE DEVICE

CROSS-REFERENCE TO RELATED APPLICATION

This application is based on and claims priority under 35 USC 119 from Japanese Patent Application No. 2011-230076 filed on Oct. 19, 2011, which is incorporated by reference herein.

BACKGROUND

1. Technical Field

The present invention relates to a radiation image capture device, and particularly relates to a radiation image capture device in which a radiation detection panel and a signal processing board are connected by a flexible printed circuit (FPC).

2. Related Art

In recent years, radiation image detectors such as flat panel detectors (FPD) and the like have been realized. In an FPD, a radiation-sensitive layer is disposed on a thin film transistor (TFT) active matrix substrate, and the FPD is capable of converting radiation directly to digital data. A radiation image capture device that uses this radiation detector has the advantage, over prior art radiation image capture devices that use X-ray films, imaging plates and the like, that images may be checked immediately. This device also has the advantage of being able to perform radioscopic imaging (video imaging) in which radiation images are successively imaged.

Diverse types of this kind of radiation detector have been proposed. For example, a radiation detector that employs an indirect conversion system converts radiation to light using a scintillator, converts the converted light to electronic charges with sensor portions such as photodiodes or the like, and accumulates these charges. The accumulated charges are information about a radiation image captured by X-ray imaging. CsI:Tl, GOS ($Gd_2O_2S$:Tb) or the like is used for the scintillator. A radiation image capture device reads out the charges accumulated in the radiation detector in the form of analog signals, amplifies the analog signals with amplifiers, and then converts the analog signals to digital data with an analog-digital (A/D) converter.

Japanese Patent Application Laid-Open (JP-A) No. 2009-257914 discloses a cassette-type radiation image detector that may prevent occurrences of failures. In this cassette-type radiation image detector, an image detection unit provided with a sensor panel, a base and a flexible cable is incorporated inside a housing. The sensor panel includes an optoelectronic conversion unit and a scintillator that converts incident radiation to light. The base is disposed to oppose the sensor panel, and is provided with a circuit relating to the optoelectronic conversion unit. The flexible cable electrically connects the optoelectronic conversion unit with the circuit, and has a chip on film (COF) structure, at which an integrated circuit component or the like is mounted, or suchlike. A side face portion of the housing that opposes the flexible cable is formed in a curved shape to match a curved form of the flexible cable. In order to release heat produced in association with operations of the integrated circuit component and the like, the flexible cable makes area contact with an inner wall portion of the curved shape of the side face portion of the housing. A housing main body of the housing is formed using carbon fibers with high thermal conductivity.

In the cassette-type radiation image detector with this structure, because the side face portion of the housing is formed in a curved shape with substantially the same curvature as the curvature with which the flexible cable is bent, even if the flexible cable vibrates, vibrations are impeded by the curved shape of the side face portion, and the flexible cable does not detach from the side face portion. Therefore, rubbing between the side face portion of the housing and the flexible cable may be prevented, and failures such as severing of wires in the flexible cable and the like due to the rubbing may be prevented.

The housing main body of the housing of the cassette-type radiation image detector disclosed in JP-A No. 2009-257914 is conductive, and the housing main body functions as an electromagnetic shield. Thus, electromagnetic noise coming from outside the cassette-type radiation image detector may be prevented. However, only very narrow gaps with dimensions of a few millimeters can be reserved between the inner wall portions of the housing main body and circuits provided at the sensor panel, the base and the like. If, in accordance with adjustments of position and posture of an imaging subject (a patient) during and before X-ray imaging, there is a touch, an impact or the like between the imaging subject and the cassette-type radiation image detector, a portion of the sensor panel or a portion of the circuits touches against the housing main body.

JP-A No. 2010-264250 discloses an X-ray imaging device that detects when irradiations of radiation start and stop and the like, and that does not require control for synchronization with radiation generation timings. In this X-ray imaging device, if a portion of a sensor panel or a portion of a circuit touches against a housing main body when there is electromagnetic noise on the housing main body, the electromagnetic noise causes changes in analog signals in the sensor panel, circuit and the like. These changes in the analog signals lead to misdetections of captured X-ray image data.

In the cassette-type radiation image detector disclosed in JP-A No. 2009-257914, in order to release heat produced in association with operations of the integrated circuit components and the like while preventing rubbing, the flexible cable makes area contact with the inner wall portion of the side face portion of the housing main body. The same as described above, when there is electromagnetic noise on the housing main body or the like, the electromagnetic noise causes changes in analog signals being propagated in the wiring of the flexible cable, leading to misdetections of captured X-ray image data.

In order to avoid misdetections of captured X-ray image data due to such electromagnetic noise, it is effective to fabricate the housing main body of a cassette-type radiation imaging device of an insulator and keep the flexible cable separated from the inner wall portion of the side face portion of the housing main body. However, although fabricating the housing main body using an insulator is effective as a measure against electromagnetic noise, when a touch, impact or the like is applied as mentioned above, the flexible cable touches or rubs against the inner wall portion of the housing main body, there is electrostatic charging of wiring in the flexible cable, and counter (compensation) charges are produced.

A method of utilizing processing software that distinguishes X-rays from noise on the basis of changes of charge amounts over time is given as a method for preventing misdetections of captured X-ray image data. When judgments are made by such processing software, the likelihood of a misdetection of X-rays when there is noise may be reduced. However, when the duration of processing by processing software is increased, there is at a reduction in workflow, an increase in losses of X-ray data during X-ray irradiation, and suchlike. Accordingly, technologies that suppress the actual production of noise are in demand.

Similarly, in an X-ray imaging device that requires control for synchronization with radiation generation timings, if electrostatic charging occurs at wiring in a flexible cable, there are changes in the analog signals during a read-out of captured X-ray image data. These changes in the analog signals appear as noise in captured X-ray images. This noise may be identified from patterns in captured X-ray images and may be corrected using processing software. However, when the duration of processing by processing software increases, time is required until display of a radiation image and the like, and there is a reduction in workflow.

SUMMARY

In consideration of the situation described above, the present invention provides a radiation image capture device that may suppress electromagnetic noise effects and suppress electrostatic charging associated with touching and rubbing caused by movements of a flexible printed circuit.

A radiation image capture device according to a first aspect includes: a radiation detection panel including optoelectronic conversion elements that convert radiation to electronic signals; a signal processing board disposed to oppose the radiation detection panel, the signal processing board performing signal processing of the electronic signals provided by the radiation detection panel; a flexible printed circuit of which one end is electrically connected to the radiation detection panel and another end is electrically connected to the signal processing board; a casing that accommodates the radiation detection panel and the signal processing board, and that accommodates the flexible printed circuit in a state of being separated from an inner wall of the casing; and a first conductor provided at a region of the flexible printed circuit that comes in contact with the casing as a result of movement of the flexible printed circuit.

BRIEF DESCRIPTION OF THE DRAWINGS

An exemplary embodiment of the present invention will be described in detail based on the following figures, wherein:

FIG. 7 is a sectional diagram showing a concrete structure of the radiation image detector shown in FIG. 2.

FIG. 10 is a sectional diagram showing a concrete structure of a radiation image detector of a radiation image capture device in accordance with a second exemplary embodiment of the present invention.

FIG. 11 is a sectional diagram showing a concrete structure of a radiation image detector of a radiation image capture device in accordance with a third exemplary embodiment of the present invention.

DETAILED DESCRIPTION

Figure 1:
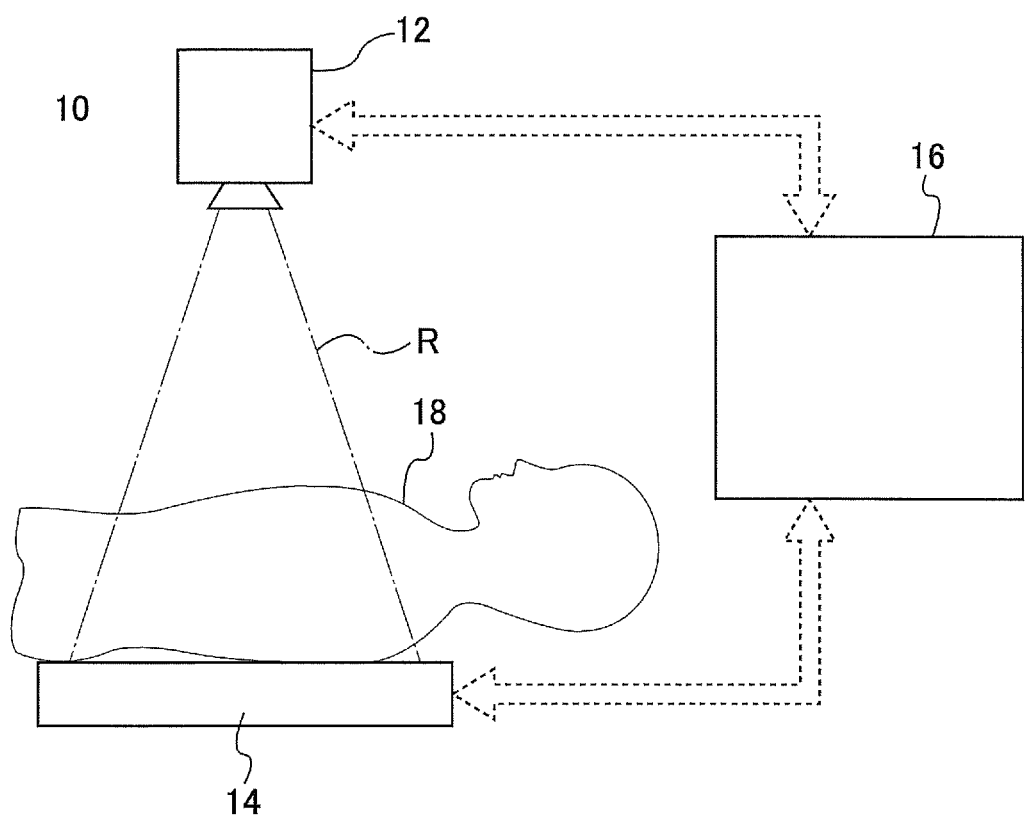
FIG. 1 is a conceptual diagram describing overall structure of a radiation image capture device in accordance with a first exemplary embodiment of the present invention.

Herebelow, exemplary embodiments in accordance with the present invention are described with reference to the attached drawings. Herein, structural elements that have the same functions are assigned the same reference numerals in the drawings, and duplicative descriptions are omitted as appropriate.

First Exemplary Embodiment

A first exemplary embodiment of the present invention illustrates an example of application of the invention to a portable radiation image detector (electronic cassette) that constitutes the radiation image capture device.

Overall Structure of the Radiation Image Capture Device

As illustrated in FIG. 1, a radiation image capture device 10 according to the first exemplary embodiment is equipped with a radiation generation device 12, a radiation image detector (electronic cassette) 14 and a console 16. The radiation generation device 12 generates radiation R and irradiates the radiation R at an imaging subject (a patient of whom a radiation image is to be captured) 18. The radiation image detector 14 generates radiation image data obtained from the radiation R transmitted through the imaging subject 18. The radiation image detector 14 is of a portable type that may be carried freely. The console 16 functions to control driving of the radiation generation device 12 and the radiation image detector 14, memorize the radiation image data generated by the radiation image detector 14, display the radiation image data, and suchlike.

In this first exemplary embodiment, the radiation image detector 14 may or may not be equipped with a function for memorizing radiation image data.

External Structure of the Radiation Image Detector

Figure 2:
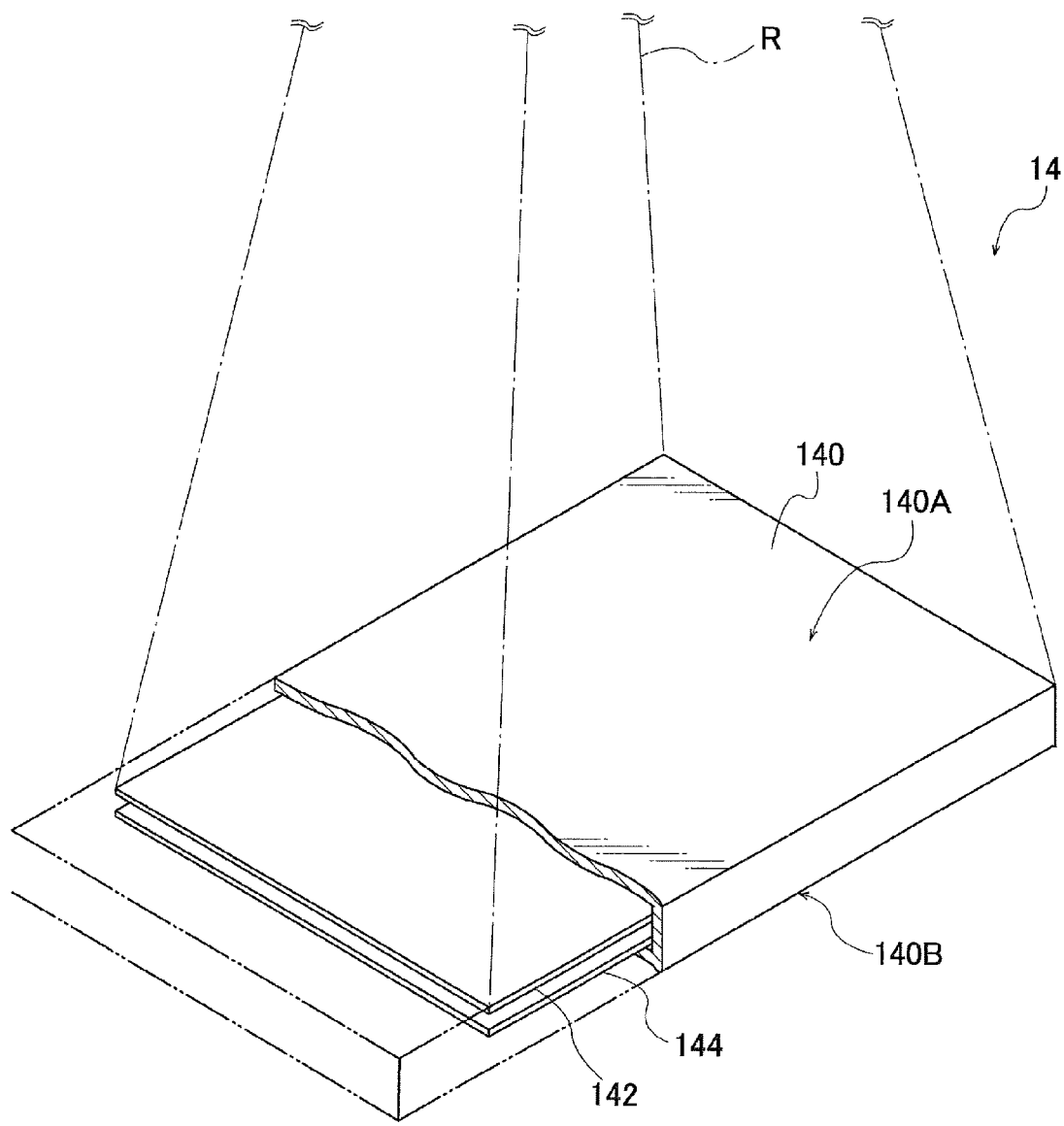
FIG. 2 is a perspective diagram of a radiation image detector (electronic cassette) of the radiation image capture device in accordance with the first exemplary embodiment, in which an appropriate portion of a casing of the radiation image detector is cut away.

As illustrated in FIG. 2, the radiation image detector 14 is provided with a casing 140 in a flat board shape with a predetermined thickness in a direction of irradiation of the radiation R. The casing 140 includes an irradiated surface 140A at the face of a side of the casing 140 that opposes the radiation generation device 12. The irradiated surface 140A is fabricated of a material that transmits at least the radiation R.

A radiation detection panel 142 and a signal processing board 144 are accommodated inside the casing 140. The radiation detection panel 142 is disposed at the irradiated surface 140A side of the casing 140, that is, the side opposing the radiation generation device 12, and the signal processing board 144 is disposed at the side of a non-irradiated surface 140B that is opposite from the irradiated surface 140A. The radiation detection panel 142 functions to generate radiation image data from the radiation R irradiated from the radiation generation device 12 and transmitted through the imaging subject 18. The signal processing board 144 functions to control driving of the radiation detection panel 142, and transmit the radiation image data generated by the radiation detection panel 142 to the console 16.

System Structure of the Radiation Image Detector

1. System Structure of the Radiation Detection Panel

Figure 3:
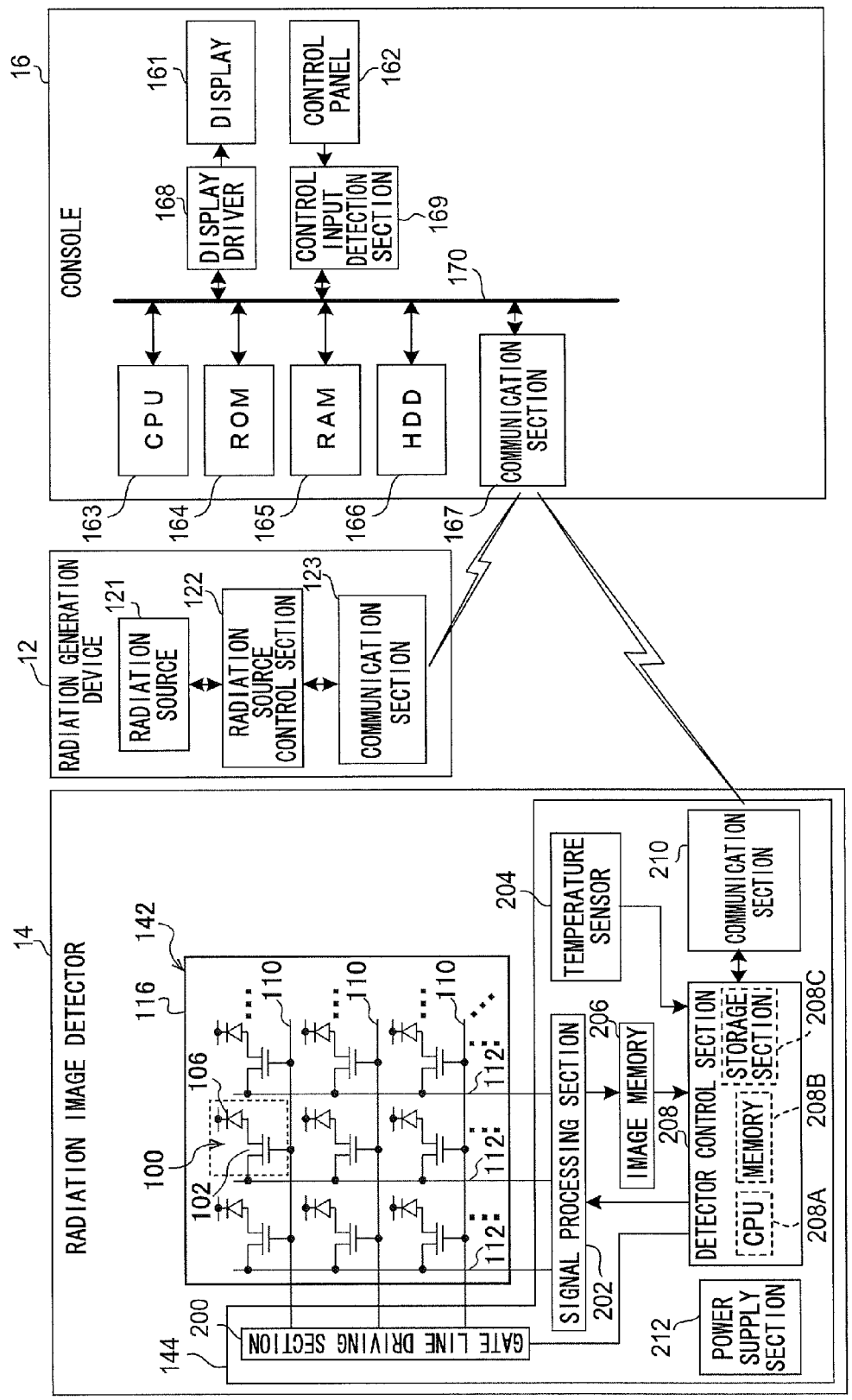
FIG. 3 is an overall block circuit diagram of the radiation image capture device in accordance with the first exemplary embodiment.

As illustrated in FIG. 3, the radiation detection panel 142 of the radiation image detector 14 is equipped with a TFT matrix board 116. The TFT matrix board 116 is provided with plural gate lines 110 and plural data lines 112. The gate lines 110 extend in a scanning line direction and are arrayed with a constant spacing in a signal line direction. The data lines 112 extend in the signal line direction and are arrayed with a constant spacing in the scanning line direction. Detection elements 100 are disposed at intersection portions of the gate lines 110 and data lines 112. Each detection element 100 detects light converted from the radiation R (radiation image data), converts the light to electronic signals, and then temporarily accumulates (stores) the electronic signals.

The detection element 100 is provided with a thin film transistor (TFT) 102 and an optoelectronic conversion element 106, and is constituted as a circuit with the TFT 102 and the optoelectronic conversion element 106 in parallel. One main electrode of the TFT 102 (the drain electrode, with reference numeral 102E in FIG. 6) is connected to the data line 112, and the other (the source electrode, with reference numeral 102D in FIG. 6) is connected with one electrode of the optoelectronic conversion element 106 (reference numeral electrode 106A in FIG. 5). The gate electrode of the TFT 102 (reference numeral 102A in FIG. 6) is connected to the data line 112. The TFT 102 is a switching element that switches between a conducting state (On) and a non-conducting state (Off) in accordance with driving signals supplied to the gate electrode. Another electrode of the optoelectronic conversion element 106 (reference numeral 106E in FIG. 5) is connected to a fixed potential. The optoelectronic conversion element 106 converts light signals, which are the radiation image data converted from the radiation R, to electronic signals and temporarily accumulates the converted radiation image data in the form of electrical charges.

2. System Structure of the Signal Processing Board

The signal processing board 144 of the radiation image detector 14 is provided with a gate line driving section 200, a signal processing section 202, a temperature sensor 204, an image memory 206, a detector control section 208, a communication section 210 and a power supply section 212.

The gate line driving section 200 is connected to the gate lines 110 extending across the TFT matrix board 116, and supplies driving signals for the TFTs 102 to the gate lines 110. According to the drawing in FIG. 3, the gate line driving section 200 is disposed along one edge of the TFT matrix board 116 (the left edge in this drawing) at the outer side of the edge. In practice, because the signal processing board 144 is disposed to oppose the radiation detection panel 142, the gate line driving section 200 is disposed along the one edge of the TFT matrix board 116 at the non-irradiated surface 140B side of the TFT matrix board 116 and is superposed with the edge.

The signal processing section 202 is connected to the data lines 112 that extend across the TFT matrix board 116, and acquires radiation image data read from the detection elements 100 via the data lines 112. Similarly to the gate line driving section 200, according to the drawing in FIG. 3, the signal processing section 202 is disposed along another edge (the lower edge in this drawing) adjoining the one edge of the TFT matrix board 116, at the outer side of the other edge. In practice, because the signal processing board 144 is disposed to oppose the radiation detection panel 142, the signal processing section 202 is disposed along the other edge of the TFT matrix board 116 at the non-irradiated surface 140B side of the TFT matrix board 116 and is superposed with the other edge. As well as the gate line driving section 200 and the signal processing section 202, components, circuits and systems mounted at the signal processing board 144 are disposed to be superposed with the TFT matrix board 116.

When a radiation image is captured and radiation image data is accumulated at the radiation detection panel 142, firstly, one of the gate lines 110 is selected using the gate line driving section 200, and a driving signal is supplied to this gate line 110. The TFTs 102 of all the detection elements 100 connected to this gate line 110 are put into the conducting state by the supply of the driving signal, and the radiation image data that has been temporarily accumulated in the optoelectronic conversion elements 106 is read out to the signal processing section 202 via the data lines 112. In the signal processing section 202, the charges are accumulated at sample-hold circuits (charge amplifiers, with reference numeral 220 in FIG. 4) that are provided in respective correspondence with the individual data lines 112.

The signal processing section 202 selects the sample-hold circuits 220 successively in the scanning line direction, and successively reads out the radiation image data accumulated in the sample-hold circuits 220. When the radiation image data accumulated at all of the detection elements 100 connected to the one selected gate line 110 has been read out, the gate line driving section 200 selects the succeeding gate line 110 in the signal line direction. By the same processing sequence, the signal processing section 202 successively selects the sample-hold circuits 220, and reads out the radiation image data accumulated at the detection elements 100 connected to this selected gate line 110. When all the radiation image data accumulated at the radiation detection panel 142 is read out, the radiation image data may be acquired as electronic signals (electronic data) captured in two dimensions.

Figure 4:
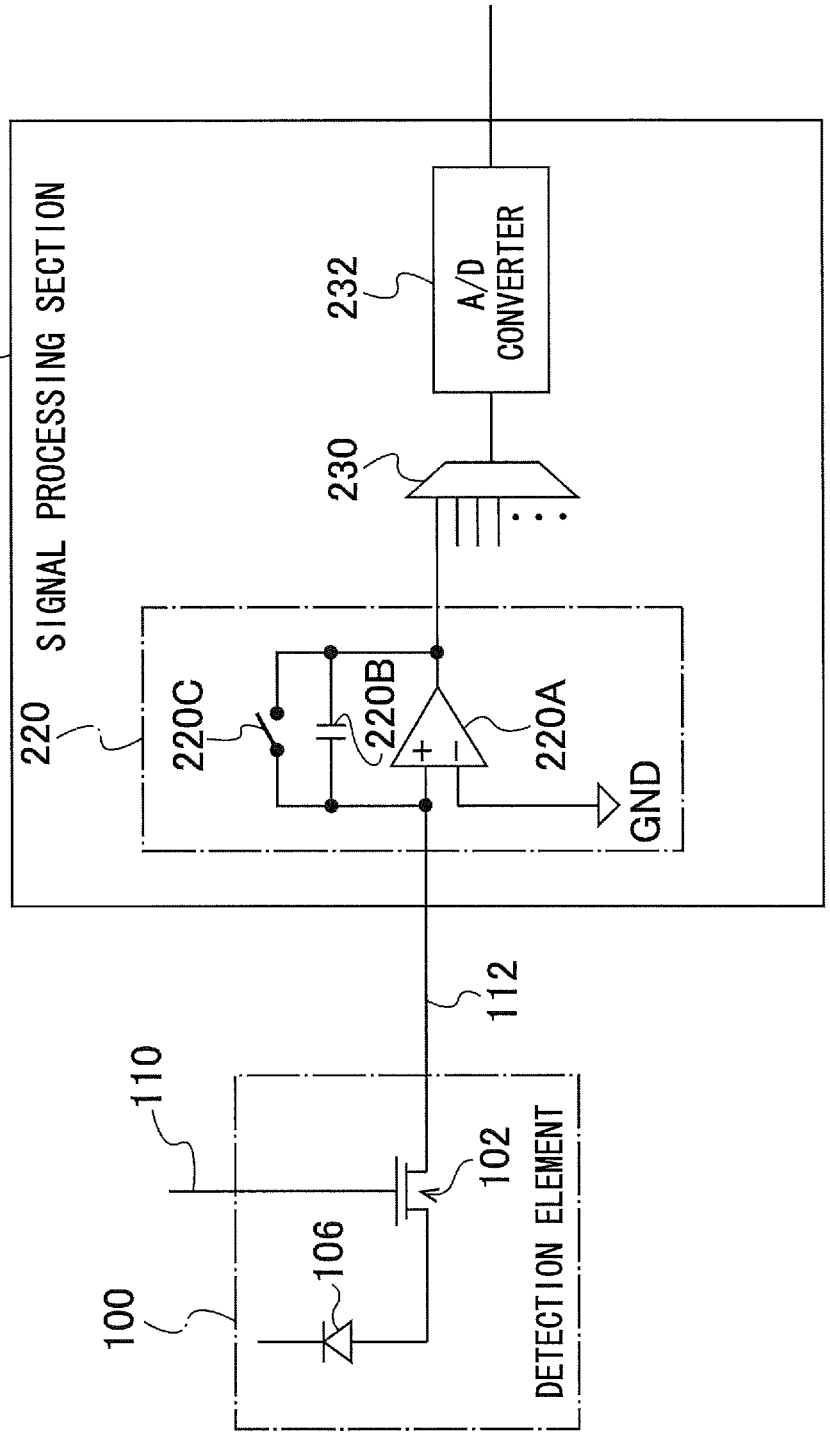
FIG. 4 is a circuit diagram of principal portions of a detection element and signal processing section of a radiation detection panel illustrated in FIG. 3.

As illustrated in FIG. 4, the signal processing section 202 is equipped with the sample-hold circuits 220, a multiplexer 230 and an analog-digital (A/D) converter 232. Each sample-hold circuit 220 is connected to the respective data line 112, and is provided with an operational amplifier 220A, a capacitor 220B and a switch 220C. The radiation image data (charge signals) propagated through the data lines 112 from the detection element 100 is retained at the sample-hold circuit 220. The sample-hold circuit 220 converts the charge signals to analog signals (voltage signals, which are the radiation image data) with the operational amplifier 220A and the capacitor 220B. That is, the sample-hold circuit 220 functions as a charge amplifier that converts the charges accumulated at the detection elements 100 to voltages. The switch 220C of the sample-hold circuit 220 is electrically connected between the electrodes of the capacitor 220B, in parallel with the capacitor 220B, and is used as a reset circuit that discharges charge signals accumulated at the capacitor 220B.

The analog signals converted at the sample-hold circuits 220 (output signals) are serially inputted to the multiplexer 230. The multiplexer 230 serially outputs analog signals to the A/D converter 232. The A/D converter 232 successively converts the serially inputted analog signals to digital signals (which are the radiation image data).

As illustrated in FIG. 3, the signal processing section 202 is connected to the image memory 206. The radiation image data converted to digital signals by the A/D converter 232 of the signal processing section 202 is serially memorized in the image memory 206. The image memory 206 is provided with a storage capacity capable of memorizing a predetermined number of frames of image data. Each time a radiation image is captured, the radiation image data obtained by the radiation image capture is sequentially stored in the image memory 206.

The detector control section 208 is connected to the gate line driving section 200, the signal processing section 202, the temperature sensor 204, the image memory 206, the communication section 210 and the power supply section 212, and administers control of the same. The detector control section 208 is equipped with a microcomputer, which is constituted with a central processing unit (CPU) 208A, memory 208B and a storage section 208C. The memory 208B is equipped with read-only memory (ROM) that stores a processing program that implements control of the radiation image detector 14, and the like, and random access memory (RAM) that temporarily stores various processing programs, data during processing and the like. The storage section 208C is constituted with non-volatile flash memory or the like that memorizes data such as the radiation image data stored in the image memory 206 and the like.

The temperature sensor 204 measures the temperature of the radiation image detector 14 and, in the first exemplary embodiment, the temperature of a central region of a lower face of the luminescent body 148 (the face at the non-irradiated surface 140B side thereof). Data on temperatures measured by the temperature sensor 204 is sent to the detector control section 208.

The communication section 210 exchanges various kinds of data with external equipment in accordance with control from the detector control section 208. The communication section 210 according to the first exemplary embodiment is a wireless communications unit complying with wireless LAN (local area network) standards, as typified by IEEE (Institute of Electrical and Electronics Engineers) 802.11a/b/g and the like. The communication section 210 transfers various kinds of data by wireless communications. Specifically, the communication section 210 exchanges various kinds of data for control relating to the capture of radiation images between the detector control section 208 and the console 16, transmits radiation image data from the detector control section 208 to the console 16, and the like.

The power supply section 212 supplies electrical power to the various circuits of the gate line driving section 200, the signal processing section 202, the image memory 206, the detector control section 208 and the communication section 210. In the first exemplary embodiment, the power supply section 212 incorporates a battery (a rechargeable battery), in order to enhance portability of the radiation image detector 14. Power is supplied from this battery to the various circuits.

When the radiation image detector 14 is not in use, the battery is connected to a power supply via an unillustrated charger and is charged up.

The radiation image detector 14 according to the first exemplary embodiment employs a non-synchronous system (a synchrony-free system) that, rather than receiving control signals and starting operation synchronously with the start of radiation image capture, detects the radiation R irradiated from the radiation generation device 12 and automatically starts operation control. The radiation R is sensed on the basis of outputs of detection sensors, with the same structure as the detection elements 100, that are embedded among the array of the detection elements 100, or outputs of detection sensors that are arrayed apart from the array of the detection elements 100. The radiation R may also be sensed on the basis of outputs of a photo sensor, using a photo sensor that detects light converted from the radiation R. Note that the present invention is not limited to the radiation image detector 14 that employs a non-synchronous system and may be applied to a radiation image detector 14 that employs a synchronous system in which the radiation image detector 14 receives control signals from the console 16 and starts operation synchronously with the start of radiation image capture.

System Structure of the Console

As illustrated in FIG. 3, the console 16 is constituted as a server computer, and is provided with a display 161 and a control panel 162. The display 161 is a monitor that displays control menus for the radiation image capture device 10, captured radiation images and the like. The control panel 162 is provided with a number of control buttons, switches and the like, and inputs various kinds of data, control instructions and the like. The console 16 is equipped with a CPU 163, ROM 164, RAM 165, a hard disk drive (HDD) 166, a display driver 168, a control input detection section 169 and a communication section 167.

The CPU 163 controls overall operations of the console 16. The ROM 164 stores various kinds of programs and the like, including a control program that controls operation of the console 16. The RAM 165 temporarily memorizes various kinds of data. The HDD 166 memorizes and retains various kinds of data. The display driver 168 controls displays of various kinds of data at the display 161. The control input detection section 169 detects operation states of the control panel 162. The communication section 167 exchanges various kinds of data such as exposure conditions and the like with the radiation generation device 12, and exchanges various kinds of data such as radiation image data and the like with the radiation image detector 14. The communication section 167 transmits and receives data by wireless communications, similarly to the communication section 210 of the radiation image detector 14.

At the console 16, the CPU 163, the ROM 164, the RAM 165, the HDD 166, the display driver 168, the control input detection section 169 and the communication section 167 are connected to one another via a system bus (a common bus line) 170. Accordingly, the CPU 163 accesses each of the ROM 164, the RAM 165 and the HDD 166 via the system bus 170. The CPU 163 also controls displays of various kinds of data at the display 161 via the system bus 170 and the display driver 168. The CPU 163 may acquire operation states of the control panel 162 by users, via the control input detection section 169 and the system bus 170 and, via the system bus 170 and the communication section 167, the CPU 163 controls exchanges of various kinds of data with each of the radiation generation device 12 and the radiation image detector 14.

System Structure of the Radiation Generation Device

As illustrated in FIG. 3, the radiation generation device 12 is provided with a radiation source 121, a radiation source control section 122 and a communication section 123. The communication section 123 exchanges various kinds of data such as exposure conditions and the like with the console 16. The radiation source control section 122 controls the radiation source 121 on the basis of exposure conditions received via the communication section 123.

The radiation source control section 122 is provided with a microcomputer similar to the detector control section 208 of the radiation image detector 14. The memory of this microcomputer stores data such as exposure conditions and the like that is received via the communication section 123. Exposure conditions include at least data such as a tube voltage, a tube current and an exposure duration. The radiation source control section 122 irradiates the radiation R from the radiation source 121 in accordance with the exposure conditions.

Apparatus Structure of the Radiation Detection Panel

1. Overall Structure of the Radiation Detection Panel

Figure 5:
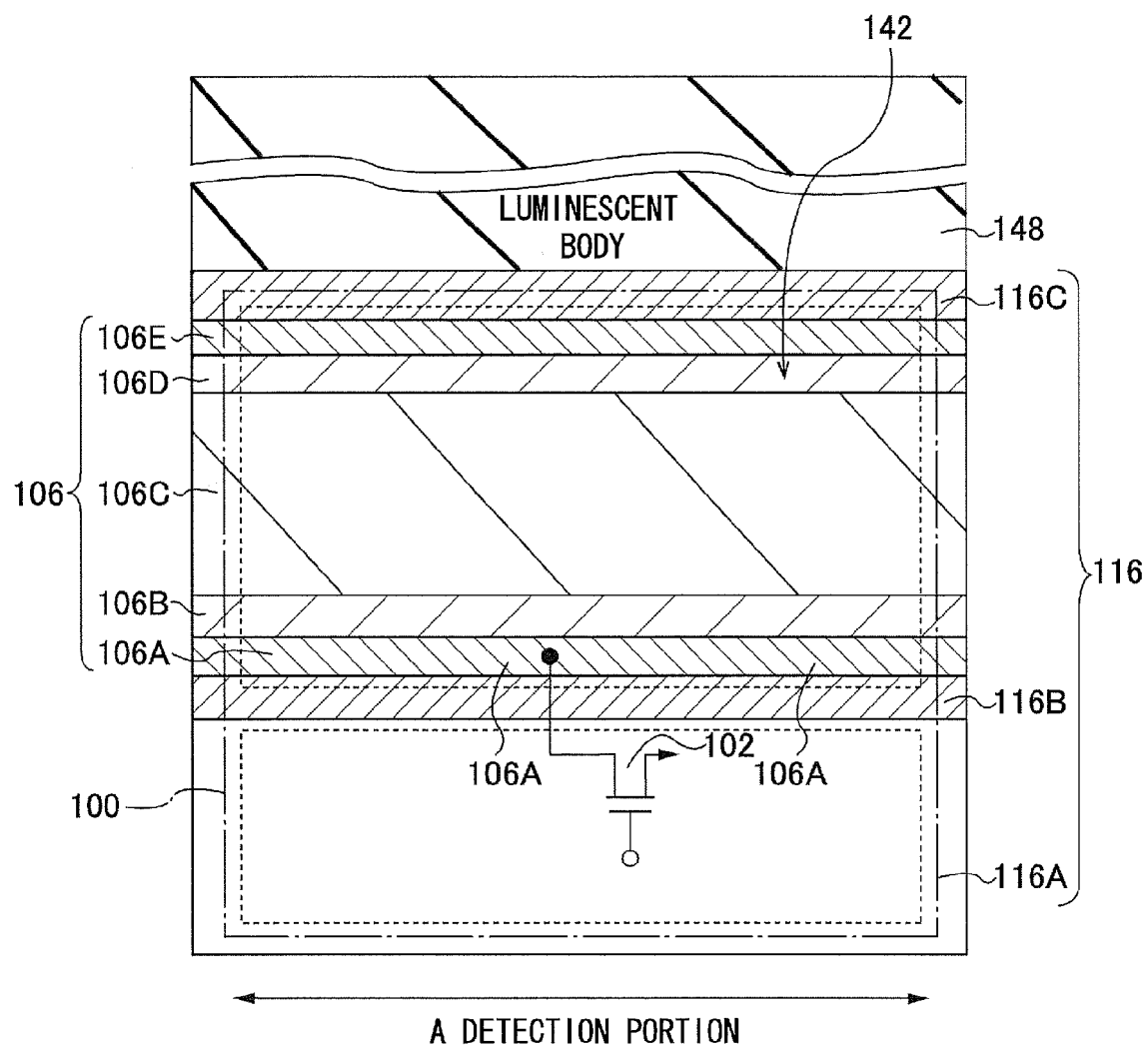
FIG. 5 is a schematic sectional diagram showing the device structure of principal portions (an optoelectronic conversion component and a luminescent body) of the radiation detection panel illustrated in FIG. 3.

As shown in FIG. 5, the radiation detection panel 142 of the radiation image detector 14 according to the first exemplary embodiment is provided with the TFT matrix board 116 and a luminescent body (scintillator) 148 that is disposed over the TFT matrix board 116 in FIG. 5. A single detection portion is appropriately illustrated in this drawing. The detection element 100 is disposed in the TFT matrix board 116. An individual detection element 100 is a single pixel, the smallest unit of resolution. The detection element 100 has a structure in which the optoelectronic conversion element 106 is provided at an insulating substrate 116A, and the optoelectronic conversion element 106 is layered on the TFT 102, which is provided on the insulating substrate 116A.

2. Structure of the Luminescent Body (Scintillator)

As shown in FIG. 5, a transparent insulating film 116C is disposed at the top layer of the TFT matrix board 116, and the luminescent body 148 is disposed over the transparent insulating film 116C. The luminescent body 148 is provided over substantially the whole area of the TFT matrix board 116. Because the luminescent body 148 is disposed over the optoelectronic conversion element 106 with the transparent insulating film 116C therebetween, radiation R that is incident from the luminescent body 148 side (the upper side of FIG. 5) may be absorbed and converted to light, and radiation R that is incident from the insulating substrate 116A side (the lower side of FIG. 5) may also be absorbed and converted to light.

A wavelength range of light emitted by the luminescent body 148 is set in accordance with the light sensitivity of the optoelectronic conversion element 106. As an example, if a photodiode or metal-insulator-semiconductor (MIS) transistor employing the commonly used amorphous silicon (a-Si) is used for the optoelectronic conversion element 106, the wavelength range is set in the visible light range (wavelengths from 360 nm to 830 nm) in accordance with the light sensitivity characteristics of the amorphous silicon. In the radiation image detector 14, if amorphous silicon is employed at the optoelectronic conversion element 106 to enable the capture of radiation images, it is preferable if the light emitted by the luminescent body 148 includes green light, at which the light sensitivity of amorphous silicon is highest.

If X-rays are used as the radiation R and X-ray images are to be captured, it is preferable if the luminescent body 148 includes caesium iodide (CsI). It is particularly preferable if cesium iodide with thallium added thereto (CsI(Tl)), which has a light emission spectrum with a wavelength range of 400 nm to 700 nm when X-rays are irradiated at the luminescent body 148, gadolinium oxysulfide (GOS; $Gd_2O_2S$:Tb) or the like is used. CsI(Tl) has a light emission peak wavelength of 565 nm in the visible light range. The radiation R of the present invention is not limited to X-rays. Radiations that may be used include at least radiations that are used in medicine, such as gamma rays, electron beams, neutron beams, proton beams, baryon beams and the like.

In the first exemplary embodiment, the luminescent body 148 is fabricated basically as a separate member (a separate body) from the TFT matrix board 116, which is the radiation detection panel 142. The luminescent body 148 is attached to the radiation detection panel 142 in a fabrication process (assembly procedure) of the radiation image detector 14.

3. Structure of the Optoelectronic Conversion Element

Figure 6:
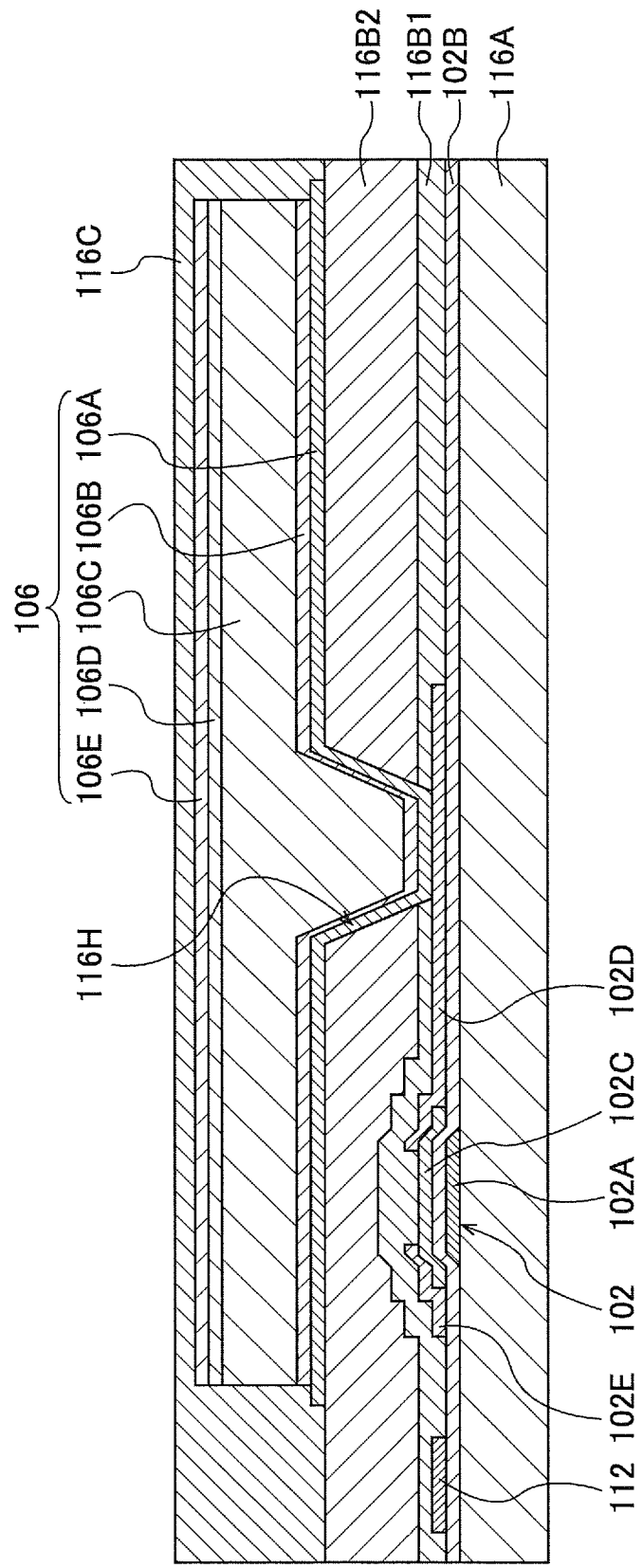
FIG. 6 is a schematic sectional diagram showing the device structure of other principal portions (a TFT and the optoelectronic conversion component) of the radiation detection panel illustrated in FIG. 3.

As shown in FIG. 5 and FIG. 6, the detection element 100 according to the first exemplary embodiment has a PIN structure, and the optoelectronic conversion element 106 that is used employs an indirect conversion system. The optoelectronic conversion element 106 is disposed on the insulating substrate 116A of the TFT matrix board 116. The optoelectronic conversion element 106 is structured by sequential layering of one electrode (a lower electrode) 106A, a first semiconductor layer 106B, a second semiconductor layer 106C, a third semiconductor layer 106D and another electrode (an upper electrode) 106E.

The electrode 106A is disposed over the insulating substrate 116A with an insulating film 116B therebetween, and is divided up between each of the detection elements 100 (each detection portion or each of pixel portions). In the first exemplary embodiment, as shown in FIG. 6, the insulating film 116B is structured by laminated films of a TFT protection film 116B1 and a flattening film 116B2 in a layer above the TFT protection film 116B1. The TFT protection film 116B1 is, for example, a SiNx film formed by chemical vapor deposition (CVD). The flattening film 116B2 is a coated insulating film formed of a photosensitive organic material with a low conductivity.

If a film thickness of the semiconductor layers from the first semiconductor layer 106B to the third semiconductor layer 106D is thick, at around 1 μm, the material of the electrode 106A is almost unrestricted in terms of transparency or non-transparency provided the material is conductive. Thus, a transparent or non-transparent conductive material may be used for the electrode 106A. As a transparent conductive material, for example, indium tin oxide (ITO) or the like may be used. As a non-transparent conductive material, for example, an aluminium film, an aluminium alloy film, a silver film or the like may be used. However, if the film thickness of the semiconductor layers from the first semiconductor layer 106B to the third semiconductor layer 106D is thin (for example, 0.2 μm to 0.5 μm), light may not be sufficiently absorbed in the first semiconductor layer 106B to third semiconductor layer 106D. The light is illuminated onto the TFT 102, and leakage current between the main electrodes 102D and 102E of the TFT 102 increases. Accordingly, it is preferable if a conductive material or laminate thereof that is non-transparent or opaque is used for the electrode 106A.

The first semiconductor layer 106B is disposed on the electrode 106A, the second semiconductor layer 106C is disposed on the first semiconductor layer 106B, and the third semiconductor layer 106D is disposed on the second semiconductor layer 106C. The optoelectronic conversion element 106 according to the first exemplary embodiment employs a PIN structure. Thus, the first semiconductor layer 106B is formed of n+-type amorphous silicon, the second semiconductor layer 106C is formed of i-type amorphous silicon, and the third semiconductor layer 106D is formed of p+-type amorphous silicon. The second semiconductor layer 106C produces charges (pairs of free electrons and free holes) from the light converted by the luminescent body 148. The first semiconductor layer 106B is used as a contact layer and is electrically connected to the electrode 106A. The third semiconductor layer 106D is similarly used as a contact layer and is electrically connected to the electrode 106E.

The electrode 106E is separately disposed on the third semiconductor layer 106D. A conductive material with high transparency such as, for example, ITO, indium zinc oxide (IZO) or the like may be used for the electrode 106E. Although not illustrated in FIG. 5 and FIG. 6, wiring that supplies a fixed potential is connected to the electrode 106E.

In the first exemplary embodiment, the optoelectronic conversion element 106 is constituted to include the electrodes 106A and 106E in addition to the first semiconductor layer 106B, second semiconductor layer 106C and third semiconductor layer 106D. The optoelectronic conversion element 106 may also employ an MIS structure.

4. Structure of the TFT

As shown in FIG. 6, the TFT 102 of each detection element 100 is disposed on the insulating substrate 116A in a region below and corresponding with the electrode 106A of the optoelectronic conversion element 106. In a plan view seen from a direction perpendicular to the surface of the insulating substrate 116A, the TFT 102 is disposed in a region superposed with the electrode 106A of the optoelectronic conversion element 106. That is, the TFT 102 and the optoelectronic conversion element 106 are laminated three-dimensionally over the insulating substrate 116A. Thus, the area of the insulating substrate 116A of each detection element 100 and the area occupied by the detection element 100 in directions in the same plane may be minimized.

The TFT 102 is provided with the gate electrode 102A, a gate insulation film 102B, an active layer (channel layer) 102C, the one main electrode (drain electrode) 102E and the other main electrode (source electrode) 102D. The gate electrode 102A is disposed on the surface of the insulating substrate 116A. In the first exemplary embodiment, the gate electrode 102A is formed in the same conductive layer as the gate lines 110, of the same conductive material. The gate insulation film 102B is disposed on the surface of the insulating substrate 116A over substantially the whole area of the insulating substrate 116A, with the gate electrodes 102A therebetween. The active layer 102C is disposed on the surface of the gate insulation film 102B and is superposed with the gate electrode 102A. The main electrodes 102D and 102E are disposed on the active layer 102C, and are separated from one another over the gate electrode 102A. In the first exemplary embodiment, the main electrodes 102D and 102E are formed in the same conductive layer of the same conductive material.

In the radiation image detector 14 according to the first exemplary embodiment, the active layer 102C of the TFT 102 is formed of amorphous silicon. The active layer 102C may also be formed of a non-crystalline oxide. An oxide containing at least one of gallium and zinc (for example, an In—O material) may be used as a non-crystalline oxide. It is preferable if an oxide containing at least two of indium, gallium and zinc (for example, an In—Zn—O material, an In—Ga—O material or a Ga—Zn—O material) is used as a non-crystalline oxide. Even more preferably, an oxide containing indium, gallium and zinc may be used. Specifically, an In—Ga—Zn—O non-crystalline oxide is preferably a non-crystalline oxide whose composition in a crystalline state would be represented by $InGaO_3(ZnO)_m$ (m being a natural number of less than 6), and more preferably $InGaZnO_4$. If the active layer 102C is formed of a non-crystalline oxide, the TFT 102 does not absorb radiation R such as X-rays or the like, or even if it does absorb such radiation R, the radiation is only retained in tiny amounts. Therefore, the production of noise may be effectively suppressed.

In the first exemplary embodiment, a non-alkaline glass is used for liquid crystals in the insulating substrate 116A. Now, if a non-crystalline oxide is employed for the active layer 102C of the TFT 102 and an organic optoelectronic conversion material is employed in place of the semiconductor layers from the first semiconductor layer 106B to the third semiconductor layer 106D of the optoelectronic conversion element 106, film formation with low temperature processes is possible for both the active layer 102C and the organic optoelectronic conversion material. Hence, the insulating substrate 116A is not limited to being a substrate with a high heat resistance, such as a semiconductor substrate, a quartz substrate, a glass substrate or the like. A flexible substrate of plastic or the like, or a substrate using an aramid (a fully aromatic polyamide), bionanofibers or the like may be employed. Specifically, a flexible substrate of a polyester such as polyethylene terephthalate, polybutylene phthalate, polyethylene naphthalate or the like, or a polystyrene, polycarbonate, polyether sulfone, polyarylate, polyimide, polycycloolefin, norbornene resin, poly(chlorotrifluoroethylene) or the like may be used. If a flexible substrate made of such a plastic is used, the radiation image detector 14 may be reduced in weight, which enhances portability for, for example, carrying, handling and the like.

On the insulating substrate 116A, the following layers may be provided: an insulating layer for ensuring insulation; a gas barrier layer for preventing permeation of moisture, oxygen and the like; an undercoating layer for improving flatness and contact with the electrodes and the like; and so forth.

An aramid that is used as the insulating substrate 116A may be an aramid that employs a high-temperature process with a temperature of 200° C. or above. Thus, the transparent electrode material is cured at a high temperature and the resistance of the high-temperature material is lowered. An automatic mounting process, including a solder reflow process with a high temperature of 200° C. or above is applicable to a driver chip constituting the gate line driving section 200. In regard to a thermal expansion coefficient of the ITO or glass plate or the like, because the thermal expansion coefficient of aramid is low, there is little warping of the insulating substrate 116A after the completion of fabrication processes, and cracks are unlikely to occur in the insulating substrate 116A. Aramid has a high mechanical strength relative to the mechanical strength of a glass plate or the like, so the insulating substrate 116A may be made thin. The insulating substrate 116A is not limited to a single-layer plate structure; a compound plate structure in which an aramid is layered on an ultra-thin glass plate may also be employed.

A bionanofiber that is used as the insulating substrate 116A may be a composite with a transparent resin of cellulose microfibril strands (bacterial cellulose) produced from a bacteria (an *Acetobacter* such as *Acetobacter Xylinum*). The cellulose microfibril strands have a microscopic width of, for example, 50 nm, which is about one tenth of the wavelengths of visible light, and have high strength, high resilience and low thermal expansion. The bacterial cellulose is immersed in a transparent resin such as an acrylic resin, an epoxy resin or the like, and the resin is cured. Thus, bionanofibers may be provided that contain 60-70% fibers and exhibit a transparency of about 90% for a wavelength of 500 nm. The bionanofibers have a low thermal expansion coefficient (3 to 7 ppm) compared with silicon crystal, have a strength comparable with steel (460 MPa) and a high resilience (30 GPa), and are flexible. Therefore, the insulating substrate 116A may be made thinner than one formed from a glass plate or the like.

The interlayer insulating film 116B is provided over the whole of the insulating substrate 116A, including the main electrodes 102D and 102E of the TFTs 102. The electrode 106A of each optoelectronic conversion element 106 is electrically connected with the main electrode 102D via a connection hole 116H formed in the interlayer insulating film 116B.

Apparatus Structure of the Radiation Image Detector

1. Overall Schematic Structure of the Radiation Image Detector

As shown in FIG. 7, the radiation image detector 14 is provided with the radiation detection panel 142, the signal processing board 144, flexible printed circuits (FPCs) 182 and 184, the casing 140, and a conductor 186. Respective one ends of the flexible printed circuits 182 and 184 are electrically connected to the radiation detection panel 142 and the other ends are electrically connected to the signal processing board 144. The casing 140 accommodates the radiation detection panel 142 and the signal processing board 144, and accommodates the flexible printed circuits 182 and 184 with a separation thereof from interior walls of the casing 140. The conductor 186 is provided at regions in which the flexible printed circuits 182 and 184 touch against the casing 140 as the result of movements of the flexible printed circuits 182 and 184.

The radiation image detector 14 according to the first exemplary embodiment employs an irradiation side sampling (ISS) system (incidence on the TFT board surface) in which light converted from the radiation R is read through the irradiated surface 140A side with respect to the radiation R. Thus, inside the casing 140, the radiation detection panel 142 is mounted at a top plate inner face at the rear side of the irradiated surface 140A, with the insulating substrate 116A shown in FIG. 5 and FIG. 6 opposing the irradiated surface 140A and the luminescent body 148 opposing the non-irradiated surface 140B. For the mounting, for example, double-sided adhesive tape is used. Note that the radiation image detector 14 is not limited to an ISS system; a scintillator face incidence system in which light converted from the radiation R is read through the non-irradiated surface 140B side, at the opposite side from the irradiated surface 140A with respect to the radiation R, may also be employed.

The radiation image detector 14 according to the first exemplary embodiment is provided with a reinforcement member 180 inside the casing 140. The reinforcement member 180 principally functions to enhance the mechanical strength of the casing 140. The reinforcement member 180 is disposed at a central region in the direction of thickness of the casing 140, and is arranged substantially in parallel with the irradiated surface 140A and non-irradiated surface 140B of the casing 140. The reinforcement member 180 is a plate-shaped member with an area a bit smaller than the irradiated surface 140A and non-irradiated surface 140B.

In the first exemplary embodiment, the reinforcement member 180 is provided with a chassis 180A, a reinforcement plate 180B and a deposition plate 180C. These are formed in a three-layer structure layered in this order from the non-irradiated surface 140B toward the irradiated surface 140A. The chassis 180A is a chassis of, for example, aluminium, whose thickness is set to 0.3 mm to 0.5 mm. The reinforcement plate 180B is a reinforcement plate of, for example, carbon, whose thickness is set to 1.1 mm to 1.3 mm. The deposition plate 180C is a deposition plate of, for example, aluminium, whose thickness is set to 0.2 mm to 0.4 mm.

The radiation detection panel 142 is disposed at the irradiated surface 140A side of the reinforcement member 180 with the luminescent body 148 therebetween. The thickness of the radiation detection panel 142 is not particularly limited, but is here set to, for example, 0.6 mm to 0.8 mm. The thickness of the luminescent body 148 is set to, for example, 0.5 mm to 0.7 mm.

The signal processing board 144 is disposed at the non-irradiated surface 140B side of the reinforcement member 180. In FIG. 7, the signal processing board 144 is schematically illustrated as a single structural element (component). In practice however, the signal processing board 144 is a wiring board at which circuits are mounted to respectively constitute the gate line driving section 200, signal processing section 202, temperature sensor 204, image memory 206, detector control section 208, communication section 210 and power supply section 212 shown in the above-described FIG. 3. The circuits include integrated circuit (chips), resistance elements, capacitance elements, condensers and the like. As an example, a printed wiring board is used for the wiring board. The circuits may be separated between and mounted on a plural number of wiring boards.

2. Structure of the Casing

As shown in FIG. 7, the casing 140 is a hollow cuboid, including the irradiated surface 140A, which is a top plate, the non-irradiated surface 140B, which is a bottom plate separated from and opposing the irradiated surface 140A, and side portions (side plates) disposed along edge portions of the irradiated surface 140A and non-irradiated surface 140B. In the radiation image detector 14 according to the first exemplary embodiment, in order to keep the effects of magnetic noise from the exterior to a minimum, at least outer side surfaces and inner side surfaces of the casing 140 are insulators. The meaning of at least the surfaces being insulators includes both the whole of the casing 140 being insulative and the main body of the casing 140 being conductive with the surfaces being made insulative (an insulating treatment being applied to the surfaces). For example, the former case corresponds to the casing 140 being fabricated of an insulating resin, and the latter case corresponds to the casing 140 being fabricated by fanning an oxide coat on the surfaces of a main body made of, for example, aluminium, the surfaces of the same kind of main body being coated with an insulating coating, or the like.

In the first exemplary embodiment, a material that may realize light weight and high stiffness is selected for the casing 140, in order to improve handling characteristics of the radiation image detector 14. In accordance with these requirements, a carbon fiber reinforced plastic (CFRP) in which carbon fiber is coated with an insulating resin is used for the casing 140. The insulating resin that is used is, for example, an epoxy resin.

3. Structure of the Flexible Printed Circuit

The flexible printed circuit 184 is a wiring cable that electrically connects the gate lines 110 of the radiation detection panel 142 with the gate line driving section 200 mounted at the signal processing board 144, as shown at the left side of FIG. 7. Although not illustrated in detail, one end of the flexible printed circuit 184 is electrically connected to external terminals of the gate lines 110 that are protruded at a periphery edge portion of the radiation detection panel 142. For the electrical connection, for example, a heat-and-pressure connection method is used in which a connection medium, such as an anisotropic conductive connector, an anisotropic conductive sheet, an anisotropic conductive film, an anisotropic conductive rubber or the like, is interposed and both heat and pressure are applied thereto. The other end of the flexible printed circuit 184 is electrically connected with external terminals of the gate line driving section 200 that are protruded at a periphery edge portion of the signal processing board 144. A heat-and-pressure connection method similar to that described above is used for this electrical connection. Only one of the flexible printed circuit 184 is illustrated in FIG. 7. In practice however, a plural number of the flexible printed circuit 184 are arrayed along the edge of the radiation detection panel 142.

A central portion of the flexible printed circuit 184 protrudes away from a side face of the radiation detection panel 142 and a side face of the signal processing board 144 toward the inner wall of a side portion of the casing 140. The central portion of the flexible printed circuit 184, utilizing its flexibility, turns around in a curve so as to describe an arc. When no external force acts on the radiation image detector 14 (when the radiation image detector 14 is in a stationary state), there are small gaps between the side faces of the radiation detection panel 142, the reinforcement member 180, and the signal processing board 144 and the inner wall of the side portion of the casing 140, at which gaps the flexible printed circuit 184 is separated from these to some extent and does not touch them. The dimensions of the spacings are set to, for example, a few millimeters.

The flexible printed circuit 184 is provided with at least a flexible (pliable) insulating film and wiring that flexibly deforms to follow the insulating film. The flexible printed circuit 184 is not limited just to use as a wiring cable; a semiconductor component may be mounted thereon. For example, a tape carrier package (TCP) may be used for the flexible printed circuit 184. Further, a chip on film (COF) or tape automated bonding (TAB) structure may be used for the flexible printed circuit 184.

As shown at the right side of FIG. 7, the flexible printed circuit 182 is a wiring cable that electrically connects the data lines 112 of the radiation detection panel 142 with the signal processing section 202 mounted at the signal processing board 144. Although not illustrated in detail, one end of the flexible printed circuit 182 is electrically connected to external terminals of the data lines 112 that are protruded at a periphery edge portion of the radiation detection panel 142. The heat-and-pressure connection method is used for this electrical connection. The other end of the flexible printed circuit 182 is electrically connected to external terminals of the signal processing section 202 that are protruded at a periphery edge portion of the signal processing board 144. The heat-and-pressure connection method is used for this electrical connection. Although only one flexible printed circuit 182 is illustrated in FIG. 7, in practice a plural number of the flexible printed circuit 182 are arrayed along another edge of the radiation detection panel 142, adjacent to the edge along which the flexible printed circuits 184 are arrayed.

Similarly to the central portion of the flexible printed circuit 184, the central portion of the flexible printed circuit 182 is curved round, utilizing its flexibility, in the interior of the casing 140. When no external force acts on the radiation image detector 14, there are small gaps between the side faces of the radiation detection panel 142, the reinforcement member 180, the signal processing board 144 and the inner wall of a side portion of the casing 140, at which gaps the flexible printed circuit 184 is separated from these to some extent and does not touch them. The dimensions of the spacings are set to, for example, a few millimeters. Thus, the flexible printed circuit 182 is similar to the flexible printed circuit 184.

If any of TCP, COF or TAB is employed at the flexible printed circuit 182, the semiconductor component (IC chip) mounted on the flexible printed circuit 182 preferably has charge amplifiers. The charge amplifiers function to amplify the radiation image data charges propagated from the data lines 112 to radiation image data voltages.

4. Structure of the Conductor

As shown in FIG. 7, the conductor 186 is provided over a surface of each of the flexible printed circuits 182 and 184, over a region L between a position of connection between the radiation detection panel 142 and the one end of the flexible printed circuit 182 or 184 and a position of connection between the signal processing board 144 and the other end of the flexible printed circuit 182 or 184. A portion of the flexible printed circuit 182 or 184 that moves (deforms) to a maximum extent when an external force (an acceleration/deceleration or vibration) is applied to the radiation image detector 14 in accordance with handling, contact with the imaging subject 18 or the like is the region that touches the inner wall of the casing 140. That is, the conductor 186 is not provided over the whole of the surface of the flexible printed circuit 182 or 184 but over a minimal partial region of the flexible printed circuit 182 or 184 that touches against the inner wall of the casing 140 (region L).

In the first exemplary embodiment, the conductor 186 is provided with a conductor (a first conductor) 186A and another conductor (a second conductor) 186B. The conductor 186A is provided on the surface of the flexible printed circuit 182 or 184 at the inner wall side of the casing 140. That is, the conductor 186A is disposed at the curved outer side surface of the flexible printed circuit 182 or 184. The conductor 186B is provided at a surface (rear face) of the flexible printed circuit 182 or 184 at the opposite side of the flexible printed circuit 182 or 184 from the side thereof that opposes the inner wall of the casing 140, over a region that touches against the reinforcement member 180. That is, the conductor 186B is disposed at the curved inner side surface of the flexible printed circuit 182 or 184. If the flexible printed circuit 182 or 184 will not touch or rub against the reinforcement member 180, it is not particularly necessary to provide the conductor 186B.

As mentioned above, the flexible printed circuit 182 or 184 includes an insulating film and wiring, and a final surface of the flexible printed circuit 182 or 184 is an ordinary protective film. The conductor 186 is not disposed between the final protective film and other portions of the flexible printed circuit 182 or 184 but is mounted in a layer above the protective film. That is, the conductor 186 is not mounted during a process of fabrication of the flexible printed circuit 182 or 184 but is mounted as a separate member after the fabrication process has been completed.

Figure 8A:
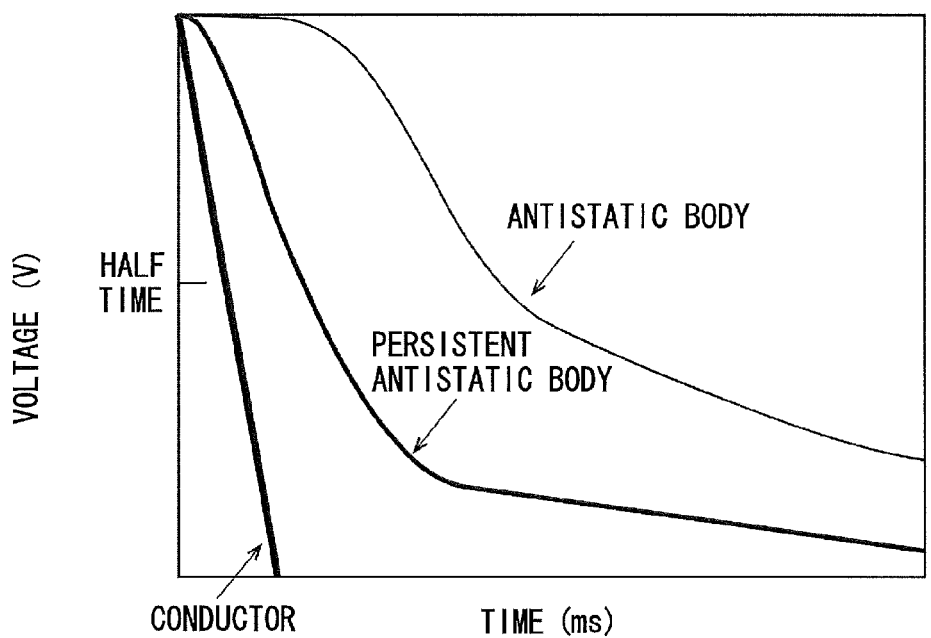
FIG. 8A is a graph showing discharge characteristics of the conductor provided at the flexible printed circuit in accordance with the first exemplary embodiment.

As illustrated in FIG. 8A, the conductor 186 (the conductors 186A and 186B) in the first exemplary embodiment is formed of a conductive material that instantly eliminates electrostatic charge voltages (charges). Moreover, the conductor 186 is formed of a material with a high enough conductivity (a low resistance value) for a quick electrostatic discharge (ESD) to occur when the conductor 186 is touched by a charged body. In FIG. 8A, the horizontal axis is time (s) and the vertical axis is voltage (V). The conductive material that is used for the conductor 186 has a surface resistivity specified as being not more than $10^5 \Omega/\cdot$. For example, any applied film (a conductive film), rubber, coating or the like containing a conductive material may be used for the conductor 186. As a film, a polymer film fabricated of polyethylene terephthalate (PET) resin is excellent in regard to flexibility. The conductor 186 may also be a metal film such as an aluminium foil, plating or the like. If the conductor 186 has adhesive functionality, the adhesion function is utilized to mount the conductor 186 on the surface of the flexible printed circuit 182 or 184, and if the conductor 186 does not have adhesive functionality, a separate adhesive material is utilized. A fixed potential 188 is electrically connected to the conductor 186 to allow electrostatic charges to escape.

If the flexible printed circuit 182 or 184 is a TCP, a board thickness of the TCP is, for example, 100 μm, and a minimum film thickness (for assuring conductivity of the conductor 186) disregarding mechanical strength of the conductor 186 is set at 25 μm. If the flexible printed circuit 182 or 184 is a COF, a board thickness of the COF is, for example, 50 μm, and the minimum film thickness disregarding mechanical strength of the conductor 186 is similarly set to 25 μm. The conductor 186 according to the first exemplary embodiment has a film thickness of the minimum film thickness or greater, and reinforces the mechanical strength of the flexible printed circuit 182 or 184. The conductor 186 is basically set to be thinner than the thickness of the flexible printed circuit 182 or 184, and functions to reinforce the mechanical strength of the flexible printed circuit 182 or 184 without impairing the flexibility.

If the flexible printed circuit 182 or 184 is any of a TCP, a COF or a TAB, a semiconductor component is mounted thereat. If a position at which the semiconductor component is disposed coincides with the region that touches the inner wall of the casing 140, the conductor 186 is provided so as to cover the semiconductor component.

Although structure is not illustrated in detail, in the first exemplary embodiment a fixed potential provided at the flexible printed circuit 182 or 184 is used for the fixed potential 188 connected to the conductor 186. The fixed potential is a ground for circuits provided at the flexible printed circuit 182 or 184 (for example, a ground or a 0 V power supply potential). The conductor 186 may be easily connected to the fixed potential 188 by this ground level being applied to the flexible printed circuit 182 or 184, the protective film on the wiring of the flexible printed circuit 182 or 184 being removed (connection holes or via holes being formed), and the wiring being connected with the conductor 186. The wiring and the conductor 186 may be electrically connected by threaded members such as screws, bolts or the like, or pins or the like. An operating power supply potential for the circuits (a power supply potential higher than 0 V) may also be used for the fixed potential. The conductor 186 may be connected to the casing 140 if the casing 140 serves as a casing earth, and may be connected to a ground of the signal processing board 144, to a ground of the radiation detection panel 142, or to the reinforcement member 180 if the reinforcement member 180 serves as a ground. Whatever is connected to thus serves as the fixed potential 188 to which the conductor 186 is connected. The fixed potential 188 may also be a fixed potential (ground or a potential other than 0 V) of an electronic circuit board other than the signal processing board 144. Further, provided the potential is fixed, a negative potential may be used for the fixed potential 188.

In the first exemplary embodiment, the conductor 186 is basically provided at every flexible printed circuit 182 or 184. In the radiation image detector 14 according to the first exemplary embodiment, misdetections of the radiation R due to electrostatic charging occur at the data lines 112 from the detection elements 100, the wiring of the flexible printed circuit 182, and lines of the signal processing section 202. Therefore, it is sufficient for the conductor 186 to be provided at least at regions of the flexible printed circuit 182 that touch or rub against the inner wall of the casing 140 or the reinforcement member 180.

Operation of the Radiation Image Capture Device

In the radiation image capture device 10 illustrated in the above-described FIG. 1, accelerations/decelerations and vibrations are applied to the radiation image detector 14 by external forces due to contacts and impacts associated with handling before imaging of a radiation image, with position adjustment and posture adjustment of the imaging subject 18 during and just before image capture, and the like. Depending on a degree of acceleration/deceleration or vibration, changes in position of the flexible printed circuits 182 and 184 in the radiation image detector 14 may be unable to follow changes in position of the rigid bodies of the radiation detection panel 142, the signal processing board 144 and the casing 140. Hence, there are movements of central portions of the flexible printed circuits 182 and 184 due to their flexibility. In accordance with such movements, the flexible printed circuits 182 and 184 touch the inner walls of the side portions of the casing 140 or are rubbed in accordance with vibrations. Amounts of movement of the flexible printed circuits 182 and 184 are larger if semiconductor components are mounted at the flexible printed circuits 182 and 184.

Counter-charging occurs at the wiring of the flexible printed circuits 182 and 184 due to this touching or rubbing. As shown in FIG. 7, each conductor 186 is provided at the region L of the flexible printed circuit 182 or 184 that touches the casing 140, and the conductor 186 is connected to the fixed potential 188. Therefore, electrostatic charges at the flexible printed circuit 182 or 184 are absorbed by the fixed potential 188 via the conductor 186.

Figure 8B:
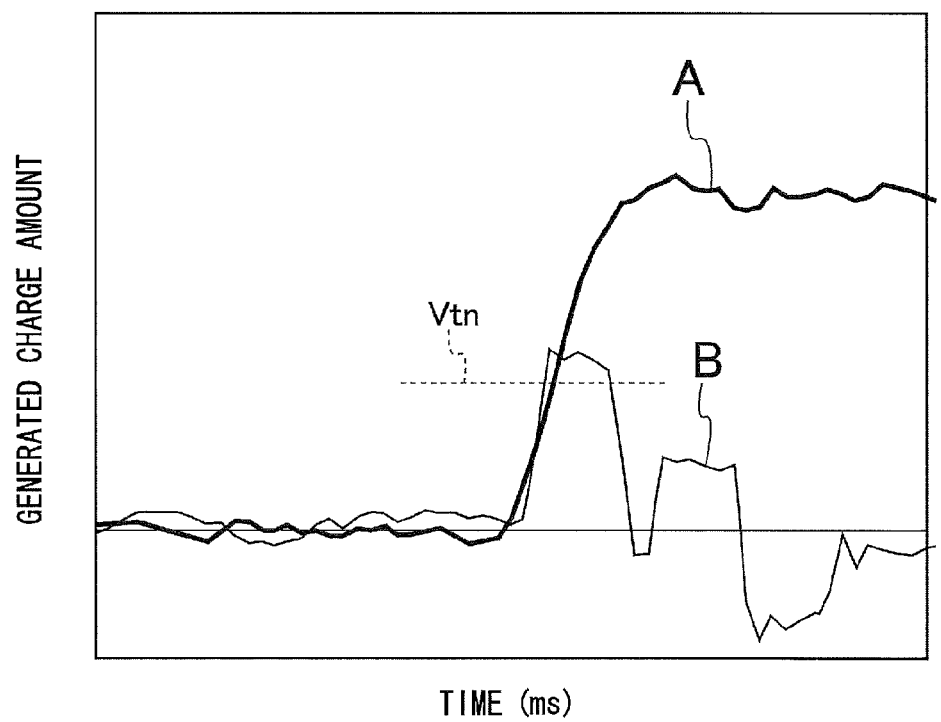
FIG. 8B is a graph showing a relationship between charge amounts flowing in wiring of the flexible printed circuit before and after an irradiation of radiation, in accordance with the first exemplary embodiment, and electrostatic charge amounts at the flexible printed circuit.

FIG. 8B shows a relationship between generated charge amounts produced in the wiring of a flexible printed circuit before and after an irradiation of radiation R and generated charge amounts produced by electrostatic charging at the flexible printed circuit. In FIG. 8B, the horizontal axis is time (ms) and the vertical axis is generated charge amounts. Graph A shows changes in charge amounts produced in the wiring of the flexible printed circuit 182 connected with the data lines 112 of the radiation detection panel 142 and the signal processing section 202 before and after the irradiation of radiation. Naturally, the charge amounts are greater after the radiation irradiation than before the radiation irradiation. Graph B shows changes in charge amounts of electrostatic charging at the wiring of the flexible printed circuit 182 caused by touches between the flexible printed circuit 182 and the casing 140, vibrations and the like in accordance with external forces acting during and just before the radiation irradiation. If a threshold $V_{th}$ for identifying a radiation R detection signal is set to the value at which the broken line is drawn in FIG. 8B, then if the wiring of the flexible printed circuit 182 is electrostatically charged and the charge amount exceeds the threshold $V_{th}$, a misdetected signal of the radiation R occurs.

Types of Casing of the Radiation Image Detector

Figure 9A:
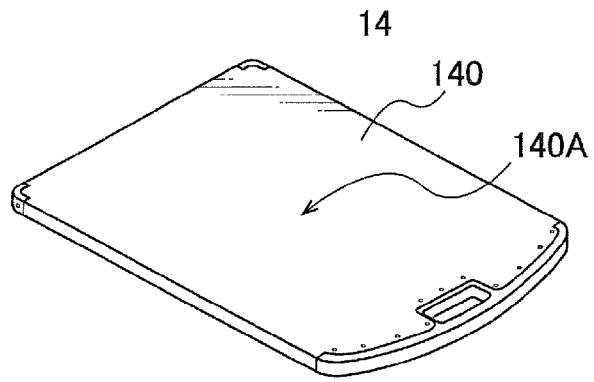
FIG. 9A is a perspective view showing a structure of the casing of the radiation image detector shown in FIG. 1.

As shown in FIG. 9A, The casing 140 of the radiation image detector 14 according to the first exemplary embodiment is formed with a frameless monocoque structure. This type of casing 140 provides the cover (front face, rear face and side faces) with the mechanical strength that a conventional frame would provide, and is suitable for reduced weight. The overall shape of this casing 140 is easily deformed by external forces, and contacts with the flexible printed circuits 182 and 184 are likely to occur. Therefore, the conductors 186 connected to the fixed potential 188 according to the first exemplary embodiment are useful in this monocoque structure.

Figure 9B:
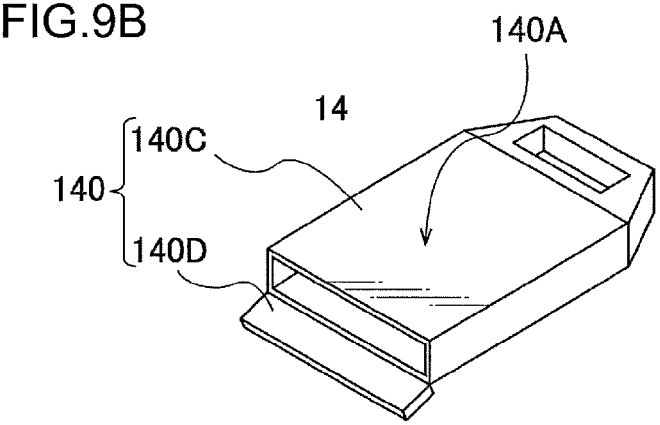
FIG. 9B is a perspective view showing another structure of the casing of the radiation image detector shown in FIG. 1.

The casing 140 shown in FIG. 9B is provided with a casing main body 140C and, at one end thereof, a lid 140D that opens and closes about a hinge. The conductive body 186 is provided at positions of a flexible printed circuit 182 or 184 that opposes the lid 140D and at positions of a flexible printed circuit 182 or 184 that opposes a side portion of the casing main body 140C at the opposite side thereof from the lid 140D.

Figure 9C:
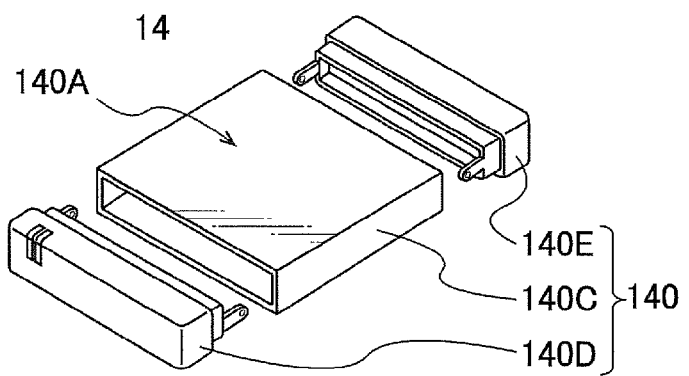
FIG. 9C is a perspective view showing a structure of the casing of the radiation image detector shown in FIG. 1.

The casing 140 shown in FIG. 9C is provided with the casing main body 140C and, at both ends thereof, lids 140D and 140E that are opened and closed by respective insertion. Arm portions protruding from each of the lids 140D and 140E engage with the inner walls of the casing main body 140C and are fixed at insertion positions. The conductors 186 are provided at positions of the flexible printed circuits 182 and 184 opposing the lids 140D and 140E.

Operational Effects of the First Exemplary Embodiment

As described hereabove, in the radiation image capture device 10 according to the first exemplary embodiment, charges produced by touching or rubbing between the flexible printed circuit 182 moving (deforming) in accordance with external forces and the inner wall of the casing 140 may be reduced by the conductor 186A. Further, charges that are produced by touching or rubbing between the flexible printed circuit 182 and the reinforcement member 180 may be reduced by the conductor 186B. Hence, the generation of noise due to electrostatic charging of the flexible printed circuit 182 may be suppressed. In addition, the conductor 186 is provided at the flexible printed circuit 182 and the mechanical strength of the flexible printed circuit 182 is supplemented by the conductor 186, and movements of the conductor 186 in accordance with external forces may be suppressed. Therefore, touching or rubbing between the conductor 186 and the inner wall of the casing 140 or the reinforcement member 180 is suppressed and actual electrostatic charging may be suppressed. Moreover, because the flexible printed circuit 182 keeps the conductor 186 away from the casing 140 when there is no external force, even if noise is occasionally produced at the casing 140, the noise may be suppressed from acting on the flexible printed circuit 182.

In the radiation image capture device 10 according to the first exemplary embodiment, charges produced by touching or rubbing between the flexible printed circuit 182 moving in accordance with external forces and the inner wall of the casing 140 or the reinforcement member 180 may be absorbed by the fixed potential 188 via the conductor 186.

In the radiation image capture device 10 according to the first exemplary embodiment, because the conductor 186 is disposed at the side of the flexible printed circuit 182 that touches against the inner wall of the casing 140, charges that are produced by touching or rubbing between the flexible printed circuit 182 moving in accordance with external forces and the inner wall of the casing 140 may be absorbed by the fixed potential 188 via the conductor 186.

In the radiation image capture device 10 according to the first exemplary embodiment, because the conductor 186 is also disposed at the opposite side of the flexible printed circuit 182 from the side thereof that opposes the inner wall of the casing 140, charges that are produced by touching or rubbing between the flexible printed circuit 182 moving in accordance with external forces and something at the opposite side of the flexible printed circuit 182 from the casing 140 inner wall side thereof (another part of the casing 140, an internal component or the like) may be absorbed by the fixed potential 188 via the conductor 186. The something at the opposite side is, for example, the reinforcement member 180.

In the radiation image capture device 10 according to the first exemplary embodiment, the conductor 186 may be fabricated easily, of any of a film, a foil, a coating or a plating.

In the radiation image capture device 10 according to the first exemplary embodiment, because the thickness of the conductor 186 is set to be thinner than the thickness of the flexible printed circuit 182, the mechanical strength of the flexible printed circuit 182 may be reinforced without the flexibility being impaired.

Second Exemplary Embodiment

A second exemplary embodiment of the present invention illustrates an example in which the structure of the conductor 186 in the radiation image detector 14 of the radiation image capture device 10 according to the first exemplary embodiment described above is altered.

Apparatus Structure of the Radiation Image Detector

As shown in FIG. 10, the radiation image detector 14 of the radiation image capture device 10 according to the second exemplary embodiment is similar to the radiation image detector 14 according to the first exemplary embodiment in that the flexible printed circuits 182 and 184 move and the conductors 186 are provided at regions of the flexible printed circuits 182 and 184 that touch or rub against the inner walls of the casing 140 or the reinforcement member 180. In the second exemplary embodiment, each conductor 186 is provided with an antistatic body (the first conductor) 186C and an antistatic body (the second conductor) 186D). The antistatic body 186C is provided at the surface at the casing 140 inner wall side of each of the flexible printed circuits 182 and 184. That is, the antistatic body 186C is disposed at the curved outer side surface of the flexible printed circuit 182 or 184. The antistatic body 186D is provided at the surface (rear face) of the flexible printed circuit 182 or 184 at the opposite side of the flexible printed circuit 182 or 184 from the side thereof that opposes the inner wall of the casing 140, over a region that touches against the reinforcement member 180. That is, the antistatic body 186D is disposed at the curved inner side surface of the flexible printed circuit 182 or 184. If the flexible printed circuit 182 or 184 will not touch or rub against the reinforcement member 180, it is not particularly necessary to provide the antistatic body 186D.

As illustrated in the previously described FIG. 8A, the antistatic bodies 186C and 186D are formed of materials that attenuate electrostatic charge voltage (charges) in short durations. The antistatic bodies 186C and 186D are formed of materials that have conductivities capable of preventing electrostatic charging thereof to a significant extent, which are conductivities capable of instantly dispersing electrostatic charges (i.e., the materials have higher resistance values than the conductors). Materials with surface resistivities specified as being between $10^9 \Omega/\cdot$ and $10^{14} \Omega/\cdot$ are used for the antistatic bodies 186C and 186D.

In the second exemplary embodiment, rather than a film in which an antistatic agent is mixed into a plastic, illustrated in FIG. 8A, a persistent antistatic body with an antistatic effect in the film itself is used for the antistatic bodies 186C and 186D. This persistent antistatic body is, for example, a film in which a metallocene catalyst-polymerized polyethylene and a polymer are blended into a metal ion-bonded resin. The persistent antistatic body functions to attenuate charges in short durations. Note that the antistatic bodies 186C and 186D are not limited to film structures and may be formed by coating of a resin containing an antistatic agent.

Each of the antistatic bodies 186C and 186D homogenizes electrostatic charges on the wiring of the flexible printed circuit 182 or 184 within the area of the antistatic body 186C or 186D (or conductor), prevents local increases in noise, and discharges the charges into moisture in the atmosphere or the like. In other words, electrostatic charges at the antistatic bodies 186C and 186D may be neutralized. Therefore, there is no need to connect the antistatic bodies 186C and 186D to the fixed potential 188, and a structure in which the antistatic bodies 186C and 186D are provided at the flexible printed circuits 182 and 184 may be simplified to the extent of structures that would connect to the fixed potential 188.

Operation of the Radiation Image Capture Device

In the radiation image capture device 10 illustrated in the above-described FIG. 10, accelerations/decelerations and vibrations are applied to the radiation image detector 14 by external forces due to contacts and impacts associated with handling before imaging of a radiation image, with position adjustment and posture adjustment of the imaging subject 18 during and just before image capture, and the like. Depending on a degree of acceleration/deceleration or vibration, the flexible printed circuits 182 and 184 touch the inner walls of the side portions of the casing 140 or are rubbed in accordance with vibrations. Furthermore, the flexible printed circuits 182 and 184 touch against the reinforcement member 180 or rub in accordance with vibrations.

Counter-charging occurs at the wiring of the flexible printed circuits 182 and 184 due to this touching or rubbing. As shown in FIG. 10, the conductor 186 is provided at regions L of the flexible printed circuits 182 and 184 that touch against the casing 140, and the conductors 186 are fabricated of the antistatic bodies 186C and 186D. Therefore, electrostatic charges at the flexible printed circuits 182 and 184 may be neutralized.

Operational Effects of the Second Exemplary Embodiment

As described hereabove, in the radiation image capture device 10 according to the second exemplary embodiment, the conductors 186 are fabricated of the antistatic bodies 186C and 186D. Therefore, in addition to the operational effects provided by the radiation image capture device 10 according to the first exemplary embodiment, charges produced by touching or rubbing between the flexible printed circuit 182 moving in accordance with external forces and the inner walls of the casing 140 may be neutralized.

In the radiation image capture device 10 according to the second exemplary embodiment, because the conductors 186 are also disposed at the opposite sides of the flexible printed circuits 182 and 184 from the sides thereof that oppose the inner walls of the casing 140, charges produced by touching or rubbing between the flexible printed circuits 182 and 184 moving in accordance with external forces and things at the opposite sides of the flexible printed circuits 182 and 184 from the casing 140 inner wall sides thereof may be released into the atmosphere. For example, charges produced at the flexible printed circuits 182 and 184 by touching or rubbing against the reinforcement member 180 may be neutralized.

In the radiation image capture device 10 according to the second exemplary embodiment, because the conductors 186 are fabricated of persistent antistatic bodies, electrostatic charges may be neutralized in short durations.

Third Exemplary Embodiment

A third exemplary embodiment of the present invention illustrates an example in which the constitution of the conductors 186 in the radiation image detector 14 of the radiation image capture device 10 according to the first exemplary embodiment or second exemplary embodiment described above is altered.

As shown in FIG. 11, the radiation image detector 14 of the radiation image capture device 10 according to the third exemplary embodiment is a combination of the radiation image detector 14 according to the first exemplary embodiment and the radiation image detector 14 according to the second exemplary embodiment, with the conductors 186 being constituted by the conductors 186A and the antistatic bodies 186D. Each conductor 186A is connected to the fixed potential 188, but each antistatic body 186D is not connected to the fixed potential 188.

With the radiation image capture device 10 according to the third exemplary embodiment, a structure that is simpler than the radiation image capture device 10 according to the first exemplary embodiment to the extent of each antistatic body 186D not being connected to the fixed potential 188 may be realized.

Figure 12:
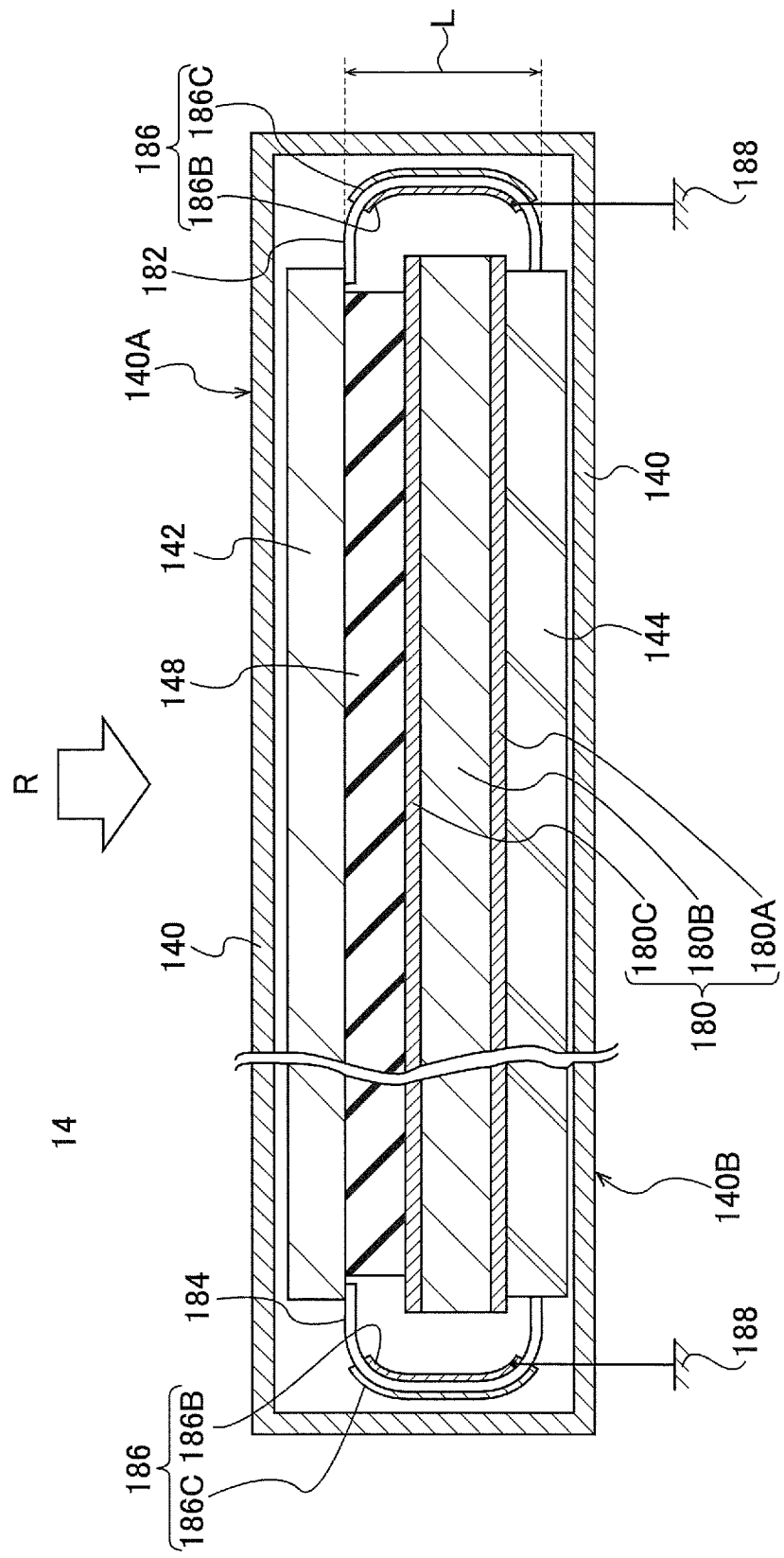
FIG. 12 is a sectional diagram showing a concrete structure of a radiation image detector of a radiation image capture device in accordance with a variant example of the third exemplary embodiment.

The radiation image detector 14 of the radiation image capture device 10 according to a variant example of the third exemplary embodiment, which is shown in FIG. 12, is the converse combination of the radiation image detector 14 according to the third exemplary embodiment, with the conductors 186 being constituted by the antistatic bodies 186C and the conductors 186B. Each antistatic body 186C is not connected to the fixed potential 188, but each conductor 186B is connected to the fixed potential 188.

With the radiation image capture device 10 according to the variant example of the third exemplary embodiment, the same operational effects may be realized as with the radiation image capture device 10 according to the third exemplary embodiment described above.

Fourth Exemplary Embodiment

A fourth exemplary embodiment of the present invention illustrates an example in which the constitution of the conductors 186 in the radiation image detector 14 of the radiation image capture device 10 according to the first exemplary embodiment described above is altered.

Figure 13:
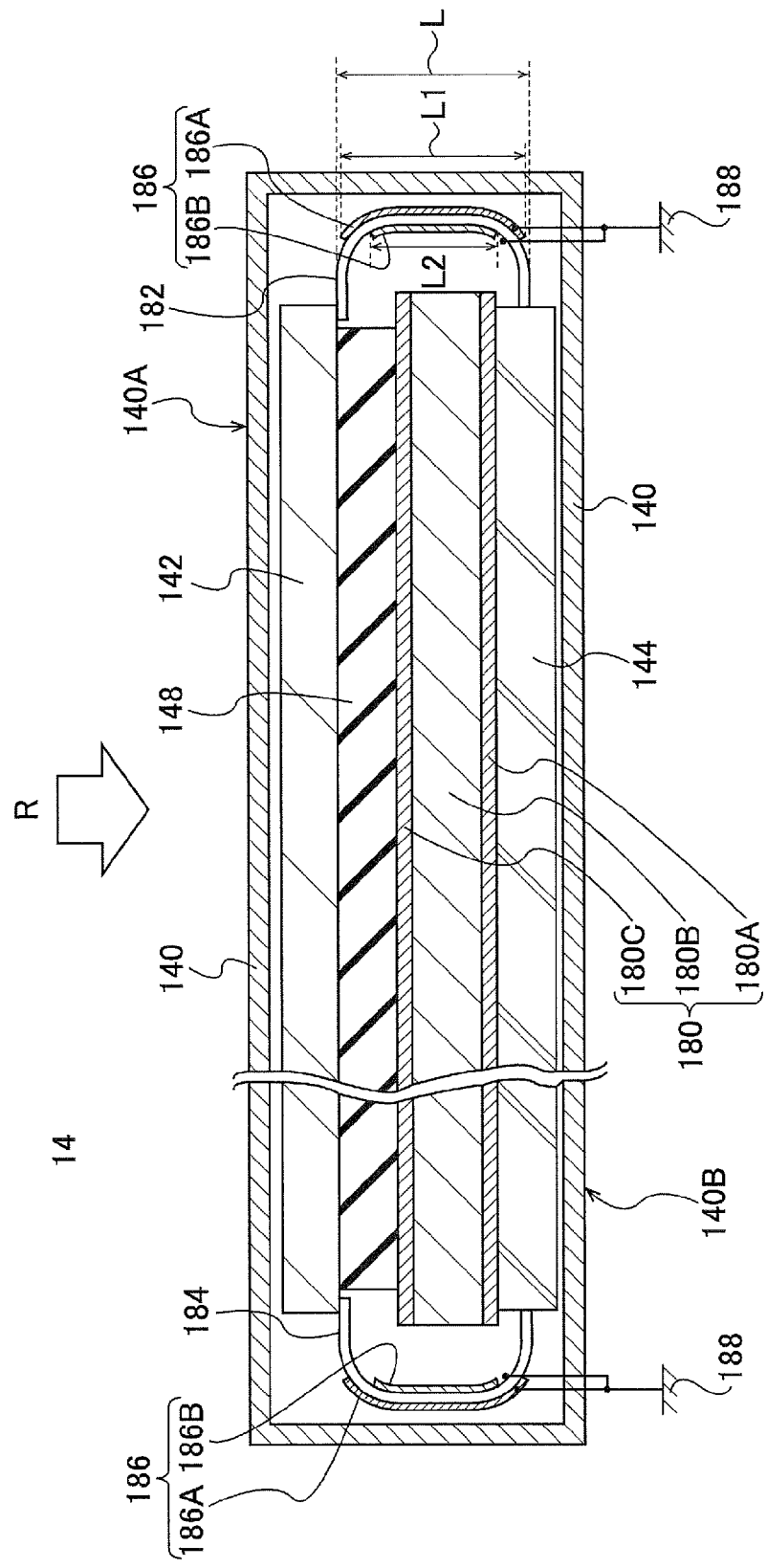
FIG. 13 is a sectional diagram showing a concrete structure of a radiation image detector of a radiation image capture device in accordance with a fourth exemplary embodiment of the present invention.

As shown in FIG. 13, in the radiation image detector 14 of the radiation image capture device 10 according to the fourth exemplary embodiment, a size L1 of the conductor 186A provided on the surface of the flexible printed circuit 182 or 184 at the casing 140 inner wall side thereof is set to be larger than a size L2 of the conductor 186B provided on the surface at the opposite side of the flexible printed circuit 182 or 184 from the casing 140 inner wall side thereof. The difference in size between the conductor 186A and the conductor 186B is formed in a direction of extension of the flexible printed circuit 182 or 184, which is specifically the up-down direction in FIG. 13 (the direction of thickness of the casing 140).

In the radiation image capture device 10 with this structure, the size of the conductor 186A provided at the casing 140 inner face side surface of the flexible printed circuit 182 or 184 is set to be larger. Therefore, in addition to the operational effects provided by the radiation image capture device 10 according to the first exemplary embodiment, charges generated at the flexible printed circuit 182 or 184 in accordance with touching or rubbing may be suppressed over a larger range of the inner wall of the casing 140. In addition, because the size of the conductor 186B provided on the surface at the opposite side of the flexible printed circuit 182 or 184 from the casing 140 inner wall side thereof is set to be smaller, the flexible printed circuit 182 or 184 may be easily curved at the inner face side while the mechanical strength of the flexible printed circuit 182 or 184 is enhanced.

The radiation image capture device 10 according to the fourth exemplary embodiment may be applied to the radiation image capture device 10 according to the second or third exemplary embodiment described above. For example, of the conductors 186 in the radiation image capture device 10 according to the second exemplary embodiment, the size of each antistatic body 186C may be made different from the size of each antistatic body 186D.

Other Embodiments

The present invention has been described above using the first to fourth exemplary embodiments, but the present invention is not limited by these embodiments. Numerous modifications are possible within a scope not departing from the spirit of the invention.

In the radiation image capture device according to the first aspect, charges that are produced by touching or rubbing between the flexible printed circuit being moved (deformed) in accordance with external forces and the inner wall of the casing may be reduced by the first conductor. Therefore, the generation of noise due to electrostatic charging of the flexible printed circuit may be suppressed. In addition, the first conductor is provided at the flexible printed circuit, the mechanical strength of the flexible printed circuit is enhanced by the first conductor, and movement of the flexible printed circuit in accordance with external forces may be suppressed. Therefore, touching or rubbing between the flexible printed circuit and the inner wall of the casing may be suppressed, and electrostatic charging itself may be suppressed. Furthermore, because the flexible printed circuit is kept away from the casing when there is an external force, even if noise is occasionally produced at the casing, the noise may be suppressed from acting on the flexible printed circuit.

In a radiation image capture device according to a second aspect, in the radiation image capture device according to the first aspect, the first conductor is connected to a fixed potential.

In the radiation image capture device according to the second aspect, in addition to the operational effects provided by the radiation image capture device according to the first aspect, charges that are produced by touching or rubbing between the flexible printed circuit moving in accordance with external forces and the inner wall of the casing may be absorbed by the fixed potential via the first conductor.

In a radiation image capture device according to a third aspect, in the radiation image capture device according to the second aspect, the first conductor is disposed over a surface of the flexible printed circuit at a side thereof that opposes the inner wall of the casing.

In the radiation image capture device according to the third aspect, the first conductor is disposed at the side of the flexible printed circuit that touches against the inner wall of the casing. Therefore, in addition to the operational effects provided by the radiation image capture device according to the second aspect, charges that are produced by touching or rubbing between the flexible printed circuit moving in accordance with external forces and the inner wall of the casing may be absorbed by the fixed potential via the first conductor.

In a radiation image capture device according to a fourth aspect, the radiation image capture device according to the third aspect further includes: a reinforcement member between the radiation detection panel and the signal processing board; and a second conductor at the opposite side of the flexible printed circuit from the side thereof that opposes the inner wall of the casing, the second conductor being provided at a region of the flexible printed circuit that comes in contact with the reinforcement member as a result of movement of the flexible printed circuit.

In the radiation image capture device according to the fourth aspect, the second conductor is disposed at the opposite side of the flexible printed circuit from the side thereof that touches against the inner wall side of the casing. Therefore, in addition to the operational effects provided by the radiation image capture device according to the third aspect, charges that are produced by touching or rubbing between the flexible printed circuit moving in accordance with external forces and the reinforcement member at the opposite side of the flexible printed circuit from the casing inner wall side thereof may be absorbed by the fixed potential via the second conductor.

In a radiation image capture device according to a fifth aspect, in the radiation image capture device according to the first aspect, the first conductor is disposed over a surface of the flexible printed circuit at a side thereof that opposes the inner wall of the casing, and the first conductor comprises an antistatic body.

In the radiation image capture device according to the fifth aspect, the first conductor comprises the antistatic body. Therefore, in addition to the operational effects provided by the radiation image capture device according to the first aspect, charges that are produced by touching or rubbing between the flexible printed circuit moving in accordance with external forces and the inner wall of the casing may be neutralized.

In a radiation image capture device according to a sixth aspect, the radiation image capture device according to the fifth aspect further includes: a reinforcement member between the radiation detection panel and the signal processing board; and a second conductor at the opposite side of the flexible printed circuit from the side thereof that opposes the inner wall of the casing, the second conductor being provided at a region of the flexible printed circuit that comes in contact with the reinforcement member as a result of movement of the flexible printed circuit, and the second conductor comprising an antistatic body.

In the radiation image capture device according to the sixth aspect, the second conductor comprises the antistatic body. Therefore, in addition to the operational effects provided by the radiation image capture device according to the fifth aspect, charges that are produced by touching or rubbing between the flexible printed circuit moving in accordance with external forces and the inner wall of the casing may be neutralized.

In a radiation image capture device according to a seventh aspect, in the radiation image capture device according to the fifth aspect or the sixth aspect, the antistatic body comprises a persistent antistatic body.

In the radiation image capture device according to the seventh aspect, the antistatic body comprises the persistent antistatic body. Therefore, in addition to the operational effects provided by the radiation image capture device according to the fifth or sixth aspect, the electrostatic charges may be neutralized in a short time.

In a radiation image capture device according to an eighth aspect, the radiation image capture device according to any of the first to third aspects further includes: a reinforcement member between the radiation detection panel and the signal processing board; and a second conductor at the opposite side of the flexible printed circuit from a side thereof that opposes the inner wall of the casing, the second conductor being provided at a region of the flexible printed circuit that comes in contact with the reinforcement member as a result of movement of the flexible printed circuit, and the second conductor comprises an antistatic body.

In the radiation image capture device according to the eighth aspect, the second conductor at the opposite side of the flexible printed circuit from the inner wall side of the casing comprises the antistatic body. Therefore, in addition to the operational effects provided by the radiation image capture device according to the first, second or third aspect, charges that are produced by touching or rubbing between the flexible printed circuit moving in accordance with external forces and the reinforcement member at the opposite side of the flexible printed circuit from the casing inner wall side thereof may be neutralized.

In a radiation image capture device according to a ninth aspect, the radiation image capture device according to the fifth aspect further includes: a reinforcement member between the radiation detection panel and the signal processing board; and a second conductor at the opposite side of the flexible printed circuit from the side thereof at which the inner wall of the casing is disposed, the second conductor being provided at a region of the flexible printed circuit that comes in contact with the reinforcement member as the result of movements of the flexible printed circuit, and the second conductor being connected to a fixed voltage.

In the radiation image capture device according to the ninth aspect, in addition to the operational effects provided by the radiation image capture device according to the fifth aspect, charges that are produced by touching or rubbing between the flexible printed circuit moving in accordance with external forces and the reinforcement member at the opposite side thereof from the inner wall side of the casing may be absorbed by the fixed potential via the second conductor.

In a radiation image capture device according to a tenth aspect, in the radiation image capture device according to the fourth, sixth, eighth or ninth aspect, a length of the first conductor in a direction of extension of the flexible printed circuit is specified to be longer than a length of the second conductor.

In the radiation image capture device according to the tenth aspect, the length of the first conductor is set to be long. Therefore, in addition to the operational effects provided by the radiation image capture device according to the fourth, sixth, eighth or ninth aspect, charges that are produced at the flexible printed circuit in accordance with touching or rubbing over a wide range of the inner wall of the casing may be suppressed. Furthermore, because the length of the second conductor is set to be small, the mechanical strength of the flexible printed circuit is enhanced, and the flexible printed circuit is easily curved at the inner wall side of the casing.

In a radiation image capture device according to an eleventh aspect, in the radiation image capture device according to the fourth aspect, the first conductor and the second conductor comprises at least one of a film, a foil, a coating or a plating.

In the radiation image capture device according to the eleventh aspect, in addition to the operational effects provided by the radiation image capture device according to the fourth aspect, the conductor may be fabricated easily, of any of a film, a foil, a coating or a plating.

In a radiation image capture device according to a twelfth aspect, in the radiation image capture device according to the fourth, sixth, eighth, ninth or tenth aspect, thicknesses of the conductors are specified to be smaller than a thickness of the flexible printed circuit.

In the radiation image capture device according to the twelfth aspect, the thicknesses of the conductors are set to be thin relative to the thickness of the flexible printed circuit. Therefore, in addition to the operational effects provided by the radiation image capture device according to the fourth, sixth, eighth, ninth or tenth aspect, the mechanical strength of the flexible printed circuit may be reinforced without impairing the flexibility.

With the configurations described above, the present invention may provide a radiation image capture device that may suppress electromagnetic noise effects and suppress electrostatic charging associated with touching and rubbing caused by movements of a flexible printed circuit.

What is claimed is:

1. A radiation image capture device comprising:
    a radiation detection panel including optoelectronic conversion elements that convert radiation to electronic signals;
    a signal processing board disposed to oppose the radiation detection panel, the signal processing board performing signal processing of the electronic signals provided by the radiation detection panel;
    a flexible printed circuit of which one end is electrically connected to the radiation detection panel and another end is electrically connected to the signal processing board;
    a casing that accommodates the radiation detection panel and the signal processing board, and that accommodates the flexible printed circuit in a state of being separated from an inner wall of the casing; and
    a first conductor provided at a region of the flexible printed circuit that comes in contact with the casing as the result of movements of the flexible printed circuit.

2. The radiation image capture device according to claim 1, wherein the first conductor is connected to a fixed potential.

3. The radiation image capture device according to claim 2, wherein the first conductor is disposed over a surface of the flexible printed circuit at a side thereof that opposes the inner wall of the casing.

4. The radiation image capture device according to claim 3, further comprising:
    a reinforcement member between the radiation detection panel and the signal processing board; and
    a second conductor at the opposite side of the flexible printed circuit from the side thereof that opposes the inner wall of the casing, the second conductor being provided at a region of the flexible printed circuit that comes in contact with the reinforcement member as the result of movements of the flexible printed circuit.

5. The radiation image capture device according to claim 4, wherein a length of the first conductor in a direction of extension of the flexible printed circuit is specified to be longer than a length of the second conductor.

6. The radiation image capture device according to claim 4, wherein at least one of the first conductor or the second conductor comprises at least one of a film, a foil, a coating or a plating.

7. The radiation image capture device according to claim 4, wherein thicknesses of the first conductor and the second conductor are specified to be smaller than a thickness of the flexible printed circuit.

8. The radiation image capture device according to claim 2, further comprising:
   a reinforcement member between the radiation detection panel and the signal processing board; and
   a second conductor at the opposite side of the flexible printed circuit from a side thereof that opposes the inner wall of the casing, the second conductor being provided at a region of the flexible printed circuit that comes in contact with the reinforcement member as a result of movement of the flexible printed circuit, and the second conductor comprising an antistatic body.

9. The radiation image capture device according to claim 1, wherein the first conductor is disposed over a surface of the flexible printed circuit at a side thereof that opposes the inner wall of the casing, and the first conductor comprises an antistatic body.

10. The radiation image capture device according to claim 9, further comprising:
    a reinforcement member between the radiation detection panel and the signal processing board; and
    a second conductor at the opposite side of the flexible printed circuit from the side thereof that opposes the inner wall of the casing, the second conductor being provided at a region of the flexible printed circuit that comes in contact with the reinforcement member as the result of movements of the flexible printed circuit, and the second conductor comprises an antistatic body.

11. The radiation image capture device according to claim 10, wherein each antistatic body comprises a persistent antistatic body.

12. The radiation image capture device according to claim 10, wherein a length of the first conductor in a direction of extension of the flexible printed circuit is specified to be longer than a length of the second conductor.

13. The radiation image capture device according to claim 10, wherein thicknesses of the first conductor and the second conductor are specified to be smaller than a thickness of the flexible printed circuit.

14. The radiation image capture device according to claim 9, wherein the antistatic body comprises a persistent antistatic body.

15. The radiation image capture device according to claim 9, further comprising:
    a reinforcement member between the radiation detection panel and the signal processing board; and
    a second conductor at the opposite side of the flexible printed circuit from the side thereof that opposes the inner wall of the casing, the second conductor being provided at a region of the flexible printed circuit that comes in contact with the reinforcement member as a result of movement of the flexible printed circuit, and the second conductor comprising an antistatic body.

16. The radiation image capture device according to claim 9, further comprising:
    a reinforcement member between the radiation detection panel and the signal processing board; and
    a second conductor at the opposite side of the flexible printed circuit from the side thereof at which the inner wall of the casing is disposed, the second conductor being provided at a region of the flexible printed circuit that comes in contact with the reinforcement member as a result of movement of the flexible printed circuit, and the second conductor being connected to a fixed voltage.

17. The radiation image capture device according to claim 16, wherein a length of the first conductor in a direction of extension of the flexible printed circuit is specified to be longer than a length of the second conductor.

18. The radiation image capture device according to claim 1, further comprising:
    a reinforcement member between the radiation detection panel and the signal processing board; and
    a second conductor at the opposite side of the flexible printed circuit from a side thereof that opposes the inner wall of the casing, the second conductor being provided at a region of the flexible printed circuit that comes in contact with the reinforcement member as a result of movement of the flexible printed circuit, and the second conductor comprising an antistatic body.

19. The radiation image capture device according to claim 18, wherein a length of the first conductor in a direction of extension of the flexible printed circuit is specified to be longer than a length of the second conductor.

20. The radiation image capture device according to claim 18, wherein thicknesses of the first conductor and the second conductor are specified to be smaller than a thickness of the flexible printed circuit.

* * * * *